United States Patent
Ogawa

(10) Patent No.: US 6,709,393 B2
(45) Date of Patent: Mar. 23, 2004

(54) ULTRASONIC RECEIVING APPARATUS AND ULTRASONIC RECEIVING METHOD

(75) Inventor: Eiji Ogawa, Kaisei-machi (JP)

(73) Assignee: Fuji Photo Film Co., Ltd., Kanagwa (JP)

( * ) Notice: Subject to any disclaimer, the term of this patent is extended or adjusted under 35 U.S.C. 154(b) by 45 days.

(21) Appl. No.: 10/390,661

(22) Filed: Mar. 19, 2003

(65) Prior Publication Data

US 2003/0187355 A1 Oct. 2, 2003

(30) Foreign Application Priority Data

Mar. 26, 2002 (JP) ........................................ 2002-086136

(51) Int. Cl.[7] .............................. A61B 8/00; A61B 8/12; A61B 8/14
(52) U.S. Cl. ........................ 600/443; 356/479; 73/603; 359/1
(58) Field of Search ................................ 600/437, 443; 73/643, 603, 606, 608, 597; 367/149; 356/477, 479, 502; 348/493, 769; 359/1, 7, 30, 32; 342/179

(56) References Cited

U.S. PATENT DOCUMENTS

| | | | |
|---|---|---|---|
| 3,836,950 A | * | 9/1974 | Bhuta et al. ................... 73/608 |
| 4,284,324 A | * | 8/1981 | Huignard et al. ................ 359/7 |
| 5,080,491 A | * | 1/1992 | Monchalin et al. .......... 356/493 |
| 5,353,262 A | * | 10/1994 | Yakymyshyn et al. ........ 367/149 |
| 5,384,573 A | * | 1/1995 | Turpin ......................... 342/179 |
| 5,450,752 A | * | 9/1995 | White et al. ................... 73/643 |
| 5,748,564 A | * | 5/1998 | Pattanayak ................... 367/149 |
| 5,796,003 A | * | 8/1998 | Sandhu et al. ................. 73/603 |
| 5,814,730 A | * | 9/1998 | Brodeur et al. ................ 73/597 |
| 5,909,279 A | * | 6/1999 | Pepper et al. ................ 356/479 |
| 6,501,551 B1 | * | 12/2002 | Tearney et al. ............. 356/477 |

FOREIGN PATENT DOCUMENTS

| | | |
|---|---|---|
| EP | 1 156 345 A2 | 11/2001 |
| JP | 2003-035660 A | 2/2003 |
| WO | WO 01/50100 A2 | 7/2001 |

OTHER PUBLICATIONS

Beard et al. An optical detection system for biomedical photoacoustic imaging. Jan. 2000. Pp. 100–109.*
Beard et al. 2D line–scan photoacoustic imaging of absorbers in a scattering tissue phantom. Jan. 2001. Pp. 34–42.*
Department of Medical Physics and Bioengineering. 2D optical ultrasound array.*
1. Takahashi et al. Underwater Acoustic sensor with Fiber Bragg Grating Optical Review vol. 4, No. 6 (1997).

(List continued on next page.)

Primary Examiner—Francis J. Jaworski
Assistant Examiner—Ruby Jain
(74) Attorney, Agent, or Firm—Sughrue Mion, PLLC

(57) ABSTRACT

An optical detection type ultrasonic receiving apparatus in which S/N ratio of the detection signal is increased while preventing the apparatus from increase of size and cost. The ultrasonic receiving apparatus includes a light source for generating broadband light, an ultrasonic detecting element including an ultrasonic sensing portion to perform intensity modulation of the light, a spectrum-separating unit for spectrum-separating the modulated light, a photo detecting unit having a plurality of photoelectric converting elements for detecting the spectrum-separated light for each of plural wavelength components to generate at least a first detection signal of a first wavelength component and a second detection signal of a second wavelength component, and processing unit for carrying out processing operation using the first detection signal and the second detection signal to obtain information about the ultrasonic wave received by the ultrasonic detecting element.

6 Claims, 16 Drawing Sheets

OTHER PUBLICATIONS

2. Uno et al., Fabrication and Performance of Fiber Optic Micro–Probe for Megahers Ultrasonic Field Measurement, T. IEE Japan, vol. 118–E, No. 11, 1998.

3. Beard et al., Transduction Mechanism of the Fabry–Perot Polymer Film Sensing Concept for Wideband Ultrasound Detection, IEEE Transaction on Ultrasonics, Ferroelectrics, and Frequency Control, vol. 46, No. 6 Nov. 1999.

P.C. Beard et al., "Optical Fiber Photoacoustic–Photothermal Probe"; Optics Letters –Optical Society of America, Aug. 1, 1998, vol. 23, No. 15, pp. 1235–1237.

S.G. Pierce et al., "Broadband Lamb Wave Measurements for Materials Characterisation", Part of the SPIE Conference on Sensory Phenomena and Measurement Instrumentation for Smart Structures and Materials, Mar. 1998, SPIE vol. 3330, pp. 92–102.

* cited by examiner

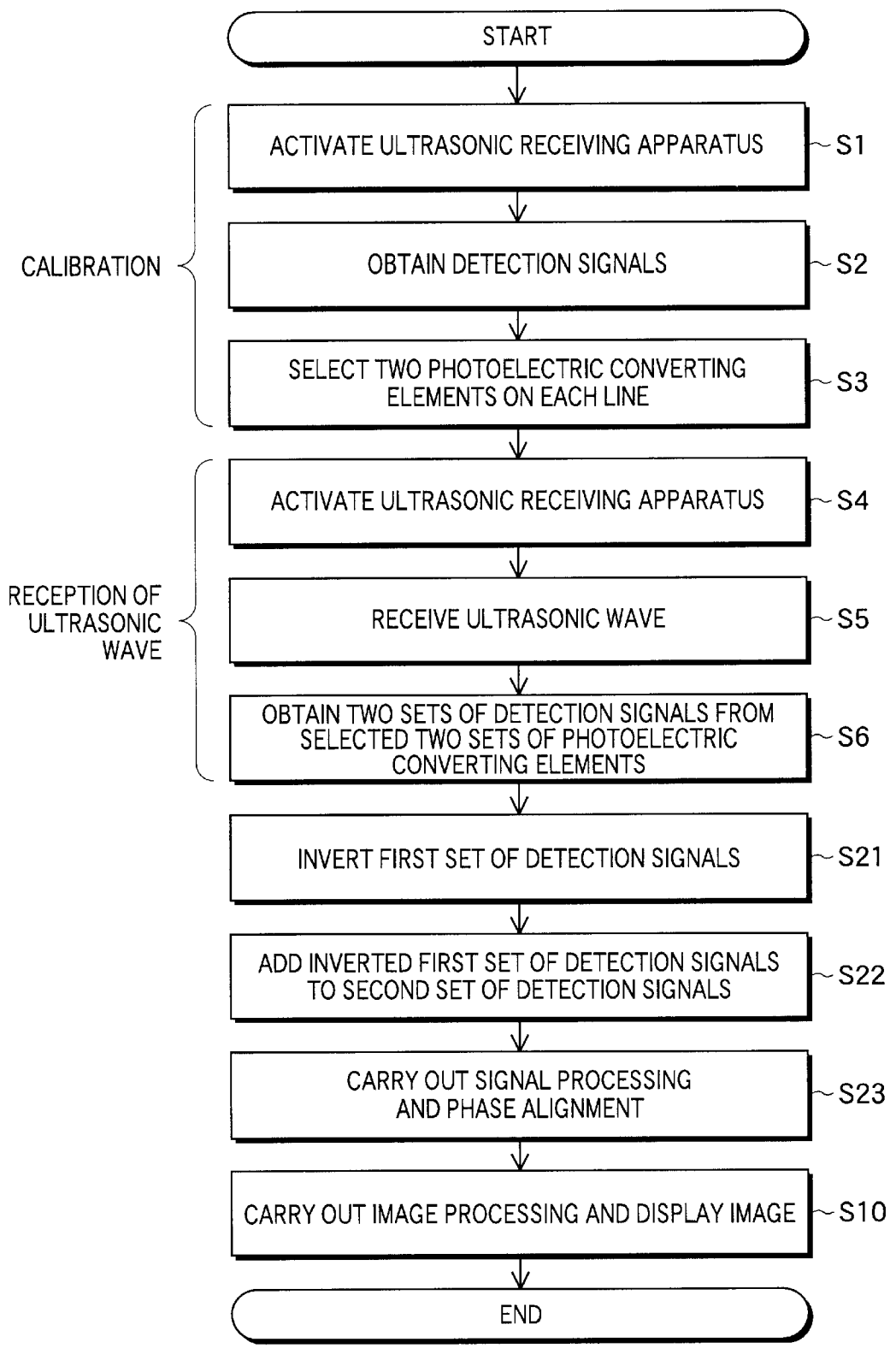

ULTRASONIC RECEIVING APPARATUS AND ULTRASONIC RECEIVING METHOD

BACKGROUND OF THE INVENTION

1. Field of the Invention

The present invention relates to an ultrasonic receiving apparatus and an ultrasonic receiving method to be used for receiving ultrasonic waves to obtain ultrasonic images.

2. Description of a Related Art

Conventionally, in an ultrasonic imaging apparatus, a one-dimensional sensor array using a piezoelectric element including a piezoelectric ceramic represented by PZT (Pb (lead) zirconate titanate) or a macromolecule piezoelectric element such as PVDF (polyvinyl difluoride) has been generally used as an element (vibrator) for transmitting and receiving ultrasonic waves. Two-dimensional images in plural cross-sections of an object to be inspected are obtained while mechanically shifting a one-dimensional sensor array as described above, and further, by synthesizing these two-dimensional images, a three-dimensional image is obtained.

However, according to this technique, since a time lag is generated in the shifting direction of the one-dimensional sensor array, cross-sectional images at different time points are synthesized resulting in blurred synthesized image. Accordingly, the technique is not suitable to such a case where images of a living organism as an object are taken in ultrasonic echo observation or the like.

In order to obtain high quality three-dimensional images using ultrasonic waves, a two-dimensional sensor capable of obtaining two-dimensional images without shifting the sensor array is required.

However, although minute processing on elements and wiring to a number of minute elements are required in the case where the two-dimensional sensor array is manufactured using the above-described PZT or PVDF, further miniaturization and integration of elements exceeding the state of the art are difficult. Also, even when the above-described problems are solved, such problems still remain that the cross talk between elements is increased, the S/N ratio is lowered due to increase of electrical impedance caused from minute wirings, electrodes of minute elements get damaged easily, and so on. Therefore, it is difficult to achieve two-dimensional sensor array using the PZT or the PVDF.

On the other hand, another type of sensor is also known, in which received ultrasonic wave signal is converted into an optical signal and then detected. As for a photo-detection type ultrasonic sensor, a sensor in which a fiber Bragg grating (abbreviated as FBG) is used (see TAKAHASHI et al., National Defense Academy "Underwater Acoustic Sensor with Fiber Bragg Grating", OPTICAL REVIEW Vol.4, No.6 (1997) p.691–694), and a sensor in which a Fabry-Perot resonator (abbreviated as FPR) structure is used (see UNO et al., Tokyo Institute of Technology "Fabrication and Performance of a Fiber Optic Micro-Probe for Megahertz Ultrasonic Field Measurement", T.IEE Japan, Vol. 118-E, No.11, (1998) p.487–492) are reported. When a two-dimensional sensor array is manufactured by using such an ultrasonic sensor as described above, the following advantages can be obtained, that is, electrical wiring to a number of minute elements is not required and satisfactory sensitivity is obtained.

Further, a photo-detection type ultrasonic sensor having a two-dimensional detection surface is also known. For example, Beard et al., University College London "Transduction Mechanisms of the Fabry-Perot Polymer Film Sensing Concept for Wideband Ultrasound Detection", IEEE TRANSACTIONS ON ULTRSONICS, FREROELECTRICS, AND FREQUENCY CONTROL, Vol.46, No.6, November1999, p.1575–1582 discloses that a polymer film having a Fabry-Perot structure is used for detecting ultrasonic waves. In a film-like ultrasonic sensor as described above, since processing on a number of minute elements is not required, the cost can be reduced. The photo-detection type ultrasonic sensor utilizes an ultrasonic detecting element having light reflection characteristics which are changed by receiving ultrasonic waves. Herein, the term "reflection characteristics" means the relationship of the reflection intensity of the light with respect to the wavelengths of the light.

However, in the ultrasonic detecting element as described-above, since the reflection characteristics of the light changes due to temperature or humidity changes, fluctuation of detection sensitivity is large. Also, in the ultrasonic detecting element having a two dimensional detection surface, the light reflection characteristics differ depending on the position of the detection surface resulting in fluctuation of the detection sensitivity. Thus, in an ultrasonic receiving apparatus to which the optical detection method is applied, it is a critical problem in practical use to control the changes or fluctuation of the detection sensitivity due to ambient factor such as temperature or structural factor. In order to solve this problem, for example, it is conceivable to adjust the wavelength of light output from a light source to a point where the sensitivity of the ultrasonic detecting element is high. However, it is difficult to adjust the wavelength of the light output from the light source with respect to extremely steep reflection characteristics. On the other hand, such method is also conceivable that a broadband light is allowed to enter ultrasonic detecting elements having different reflection characteristics depending on the position and the reflected light is separated by a filter. However, in this case, such problem remains that the structure of the ultrasonic detecting elements becomes complicated resulting in a higher cost. Furthermore, although such method is also conceivable that the reflection characteristics are made to be different from each other depending on each detection area of the ultrasonic detecting element, in this case also, the structure of the ultrasonic detecting element becomes complicated resulting in a higher cost.

In order to increase the detection sensitivity in the ultrasonic receiving apparatus as described above, for example, it is conceivable to increase the inclination of the optical reflectance in the light reflection characteristics of the ultrasonic detecting elements, or to increase the compliance of an ultrasonic sensor upon receiving the ultrasonic wave. However, when the inclination of the optical reflectance in the reflection characteristics is increased, a strict adjustment accuracy of the wavelength of the light used for detection is also required. On the other hand, in order to increase the compliance of the ultrasonic sensor, a softer member may be used for the ultrasonic receiving surface of the ultrasonic sensor. However, owing to this, temperature-dependency of the reflection characteristics in the ultrasonic sensor is also increased resulting in an unstable detection operation.

SUMMARY OF THE INVENTION

The present invention has been achieved in view of the above-described problems. An object of the present invention is, in an optical detection type ultrasonic receiving apparatus and an ultrasonic receiving method, to increase the S/N ratio and the like of the detection signal while preventing the apparatus from getting larger in size and the cost thereof from increasing.

In order to solve the above-described problems, an ultrasonic receiving apparatus according to the present invention comprises a light source for generating broadband light, an ultrasonic detecting element including an ultrasonic sensing portion which is expanded and contracted by a received ultrasonic wave to change an optical reflectance thereof in accordance with expansion and contraction thereby performing intensity modulation of the light generated by the light source, spectrum separating means for spectrum-separating the light intensity-modulated by the ultrasonic detecting element, photo detecting means having a plurality of photoelectric converting elements for detecting the light spectrum-separated by the spectrum separating means for each of the plural wavelength components to generate at least a first detection signal obtained by detecting a first wavelength component and a second detection signal obtained by detecting a second wavelength component, and processing means for carrying out processing operation using the first detection signal and the second detection signal so as to obtain information about the ultrasonic wave received by the ultrasonic detecting element.

Herein, the above-described spectrum separating means may spectrum-separate the plural light beams guided from the plural detection areas of the ultrasonic detecting element in bulk. Also, the above-described photo detecting means may detect the plural light beams which are spectrum-separated by the spectrum separating means with respect to the respective wavelengths.

An ultrasonic receiving method according to the present invention comprises steps of (a) allowing light to enter an ultrasonic detecting element including an ultrasonic sensing portion which is expanded and contracted by a received ultrasonic wave to change an optical reflectance thereof in accordance with expansion and contraction thereby performing intensity modulation of the incident light, spectrum-separating the light intensity-modulated by the ultrasonic detecting element and detecting the spectrum-separated light for each of plural wavelength components by using photo detecting means having a plurality of photoelectric converting elements to generate at least a first detection signal obtained by detecting a first wavelength component and a second detection signal obtained by detecting a second wavelength component with respect to each of plural detection areas of the ultrasonic detecting element, and (b) carrying out processing operation using the first detection signal and the second detection signal so as to obtain information about the ultrasonic wave received at each of the plural detection areas of the ultrasonic detecting element.

Herein, step (b) may include adding the first detection signal and the second detection signal to each other after inverting the phase of either one thereof.

According to the present invention, since the processing is carried out on the basis of the plural detection signals obtained by detecting the plural wavelength components of the modulated light by using the ultrasonic detecting element, the S/N ratio or the like of the detection signals can be increased.

BRIEF DESCRIPTION OF THE DRAWINGS

FIG. 13 is the flowchart showing the operation of the ultrasonic imaging apparatus including the ultrasonic receiving apparatus according to the second embodiment of the present invention;

DESCRIPTION OF THE PREFERRED EMBODIMENTS

Figure 1:
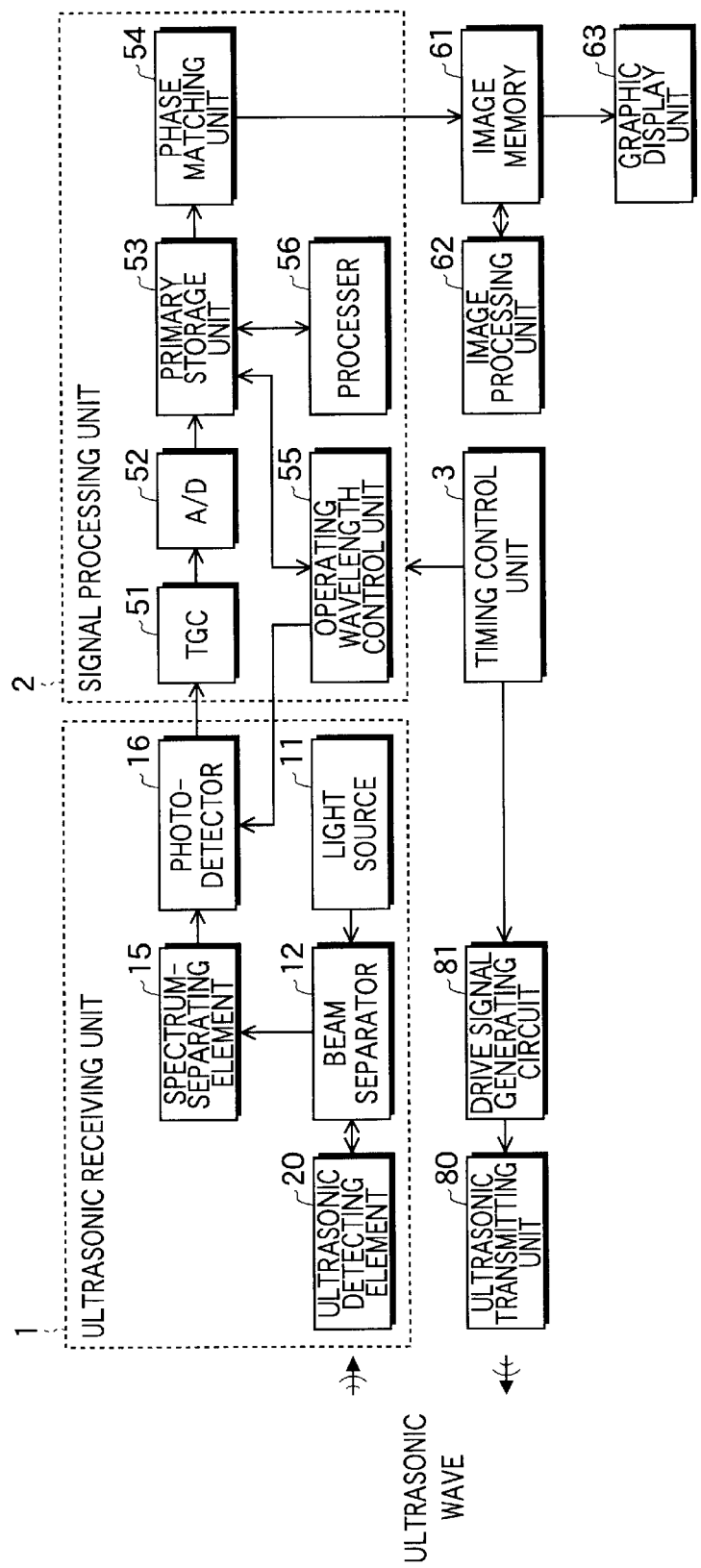
FIG. 1 is a block diagram showing a configuration of an ultrasonic imaging apparatus to which an ultrasonic receiving apparatus according to a first embodiment of the present invention is applied.

Now, referring to the drawings, embodiments of the present invention will be described in detail. The same component elements will be given with the same reference numerals and the descriptions thereof will be omitted.

FIG. 1 is a block diagram showing an ultrasonic imaging apparatus to which an ultrasonic receiving apparatus according to a first embodiment of the present invention is applied. The ultrasonic receiving apparatus comprises an ultrasonic receiving unit 1 for receiving ultrasonic waves to output detection signals, a signal processing unit 2 for processing detection signals output from the ultrasonic receiving unit 1, and a timing control unit 3. The ultrasonic imaging apparatus further comprises an image memory (secondary storage unit) 61, an image processing unit 62, a graphic display unit 63, an ultrasonic transmitting unit 80, and a drive signal generating circuit 81.

The ultrasonic receiving unit 1 includes a light source 11, a beam separator 12, an ultrasonic detecting element 20, a spectrum-separating element 15, and a photodetector 16. The ultrasonic receiving unit 1 converts a received ultrasonic signal into an optical signal and transmits the same, and further, converts the optical signal into a detection signal, which is an electrical signal, and outputs the same. The photodetector 16 has a plurality of photoelectric converting elements for detecting plural spectrum-separated wavelength components corresponding to respective areas of the ultrasonic detecting element 20. The constitution of the ultrasonic receiving unit 1 will be described later in detail.

The signal processing unit 2 includes a TGC (time gain compensation) amplifier 51, an A/D converter 52, a primary storage unit 53, a phase matching unit 54, an operating wavelength control unit 55 and a processor 56. The signal processing unit 2 processes the detection signal output from the ultrasonic receiving unit 1 to generate a signal representing information such as intensity of an ultrasonic wave at a plurality of detection areas of the ultrasonic receiving unit 1.

The TGC amplifier 51 adjusts the attenuation of the ultrasonic wave within an object to be inspected by amplifying the detection signal output from the photodetector 16 while changing the gain corresponding to the detection time. The A/D converter 52 converts detection signals into digital signals (data). The primary storage unit 53 stores these signals in chronological order. The phase matching unit 54 performs processing operation based on the data stored in the primary storage unit 53 to adjust the phase.

When a calibration is carried out before receiving ultrasonic wave, the operating wavelength control unit 55 decides, on the basis of the signal output from the photodetector 16, as to which photoelectric converting elements should be selected from among the plurality of photoelectric converting elements corresponding to each detection area of the ultrasonic detecting element 20 for detecting the ultrasonic wave. According to the present invention, plural detection signals are used corresponding to one detection area. In the first embodiment, two photoelectric converting elements are selected corresponding to one detection area in order to obtain a first detection signal and a second detection signal. Accordingly, corresponding to plural detection areas, a plurality of first photoelectric converting elements and a plurality of second photoelectric converting elements, that is, two sets of photoelectric converting elements are selected. Also, upon receiving ultrasonic waves, the operating wavelength control unit 55 controls the photodetector 16 or the signal processing unit 2 so that the detection signals, which are output from the selected two sets of photoelectric converting elements, are stored in the primary storage unit 53.

Further, the processor 56 performs processing operation by using two sets of detection signals (data) stored in the primary storage unit 53 to obtain intensity or the like of the ultrasonic wave.

The image memory (secondary storage unit) 61 stores plural plane data based on phase-aligned data. The image processing unit 62 reconstitutes two-dimensional data or three-dimensional data on the basis of these data, and performs interpolation, response modulation processing and gradation processing and so on. The graphic display unit 63 is a display apparatus, for example, such as a CRT or LCD, which displays images based on these processed image data.

The drive signal generating circuit 81 generates a drive signal for transmitting ultrasonic wave. The ultrasonic transmitting unit 80 transmits an ultrasonic wave in accordance with the drive signal generated from the drive signal generating circuit 81. The ultrasonic transmitting unit 80 comprises, for example, a vibrator in which an electrode is formed on a piezoelectric element. The piezoelectric element includes a material having piezoelectric characteristics such as a piezoelectric ceramic represented by PZT (Pb (lead) zirconate titanate) or a macromolecule piezoelectric element represented by PVDF (polyvinyl difluoride). When a voltage is applied to the electrode of the vibrator from the drive signal generating circuit 81 by providing a pulse-like electric signal or a continuous wave electric signal, the piezoelectric element expands and contracts due to the piezoelectric effect. Owing to this, ultrasonic pulses or continuous ultrasonic waves are generated from the vibrator.

The timing control unit 3 controls the drive signal generating circuit 81 so as to generate a drive signal at a predetermined timing, and controls the signal processing unit 2 so as to take in a detection signal output from the photodetector 16 when a predetermined time has passed after the transmission time.

The ultrasonic detecting element 20 and the ultrasonic transmitting unit 80 may be disposed separately as shown in FIG. 1. Alternatively, an ultrasonic probe may be formed by combining the ultrasonic detecting element 20 and the ultrasonic transmitting unit 80.

Figure 2:
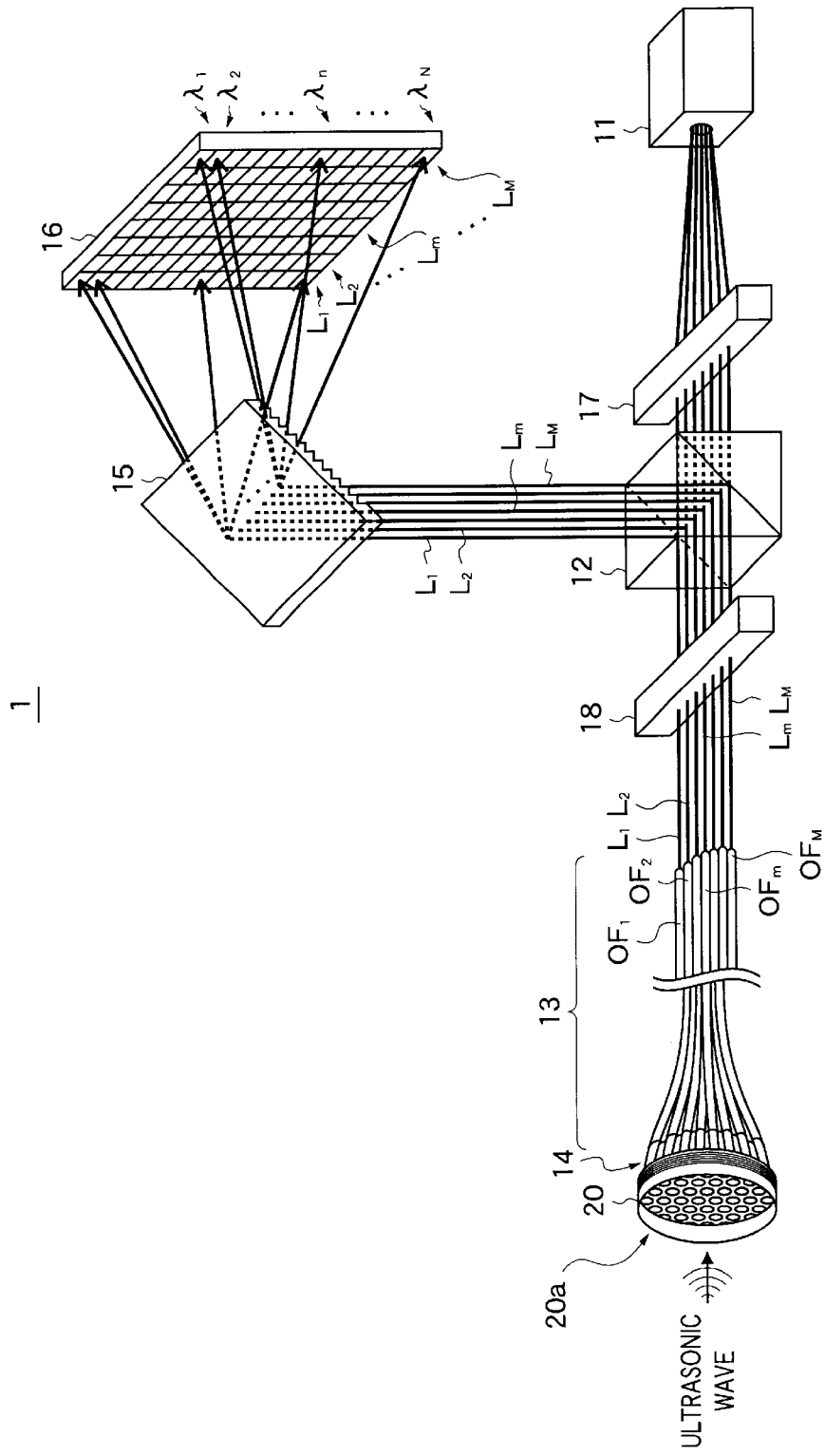
FIG. 2 is a schematic diagram illustrating the constitution of an ultrasonic receiving unit as shown in FIG. 1.

FIG. 2 is a schematic diagram illustrating the constitution of the ultrasonic receiving unit 1 as shown in FIG. 1. The ultrasonic receiving unit 1 further includes a collimator lens 17 that makes the light emitted from the light source 11 into parallel light beams and guides the same to the beam separator, and a collimator lens 18 that makes light reflected from the ultrasonic detecting element 20 into parallel light beams and guides the same to the beam separator. Also, optical transmission path 13 and collimating portion 14 are provided to guide the light beam between the collimator lens 18 and the ultrasonic detecting element 20.

Hereinafter, the relationship between the wavelength of the light beam and the reflection intensity of the light beam in the ultrasonic detecting element 20 will be referred to as reflection characteristics.

As for the light source 11, it is preferred to use a light source having a bandwidth that can cover a range exceeding the inclined band of the reflection characteristics. As a light source that generates broadband light beam as described above, for example, an LED (light emitting diode), an SLD (supper luminescent diode), ASE (Amplified Spontaneous Emission) light source, an LD (laser diode) which has a relatively large beam width, or the like is applicable.

The beam separator 12 comprises a half mirror, an optical circulator, a polarizing beam splitter or the like. The beam separator 12 allows an incident light that enters from a first direction to pass through to a second direction, and reflects the light returned from the second direction toward a third direction different from the first direction. In the first embodiment, a half mirror is used as the beam separator 12. The half mirror allows the incident light to pass through in the direction opposite to the incident direction, and reflects the light returned from a direction opposite to the incident direction toward the direction substantially perpendicular to the incident direction.

The optical transmission path 13 guides the light, which has passed through the beam separator 12, to the ultrasonic detecting element 20. As for the optical transmission path 13, a bundle fiber, in which a number of optical fibers (for example, 1024 fibers) are bundled, is used. FIG. 2 shows optical fibers $OF_1$–$OF_M$ disposed on a line. As shown in FIG. 2, a number of optical fibers are bundled into a configuration in accordance with the receiving surface (for example, a circular configuration) at the ultrasonic detecting element side (left side in the figure) and are disposed on a line at the beam separator 12 side (right side in the figure). Alternately, optical fibers disposed on a line may be piled up into several layers.

The front end of the optical transmission path 13 is connected to the ultrasonic detecting element 20 via the collimating portion 14 with the optical axes thereof aligned with each other. The collimating portion 14 includes, for example, a collimator lens array in which a plurality of collimator lenses are arrayed. The constitution of the optical transmission path 13 and the collimating portion 14 will be described later in detail.

The ultrasonic detecting element 20 has a two-dimensional receiving surface 20a, which is distorted by propagated ultrasonic wave, and an ultrasonic sensing portion which is expanded and contracted corresponding to the ultrasonic wave received by the receiving surface 20a. Since an optical reflectance of the ultrasonic sensing portion changes in correspondence with the expansion and contraction, the light entered the ultrasonic detecting element 20 via the optical transmission path 13 and the collimating portion 14 is subjected to intensity modulation and then reflected.

The spectrum-separating element 15 comprises, for example, a diffraction grating, a prism or the like and outputs the incident light in the different directions in accordance with wavelength thereof. That is, the spectrum-separating element 15 spectrum-separates the light beams $L_1$–$L_M$, which are output parallel from the optical fibers $OF_1$–$OF_M$, and guides a plurality of spectrum-separated light beams to the photodetector 16.

Figure 3:
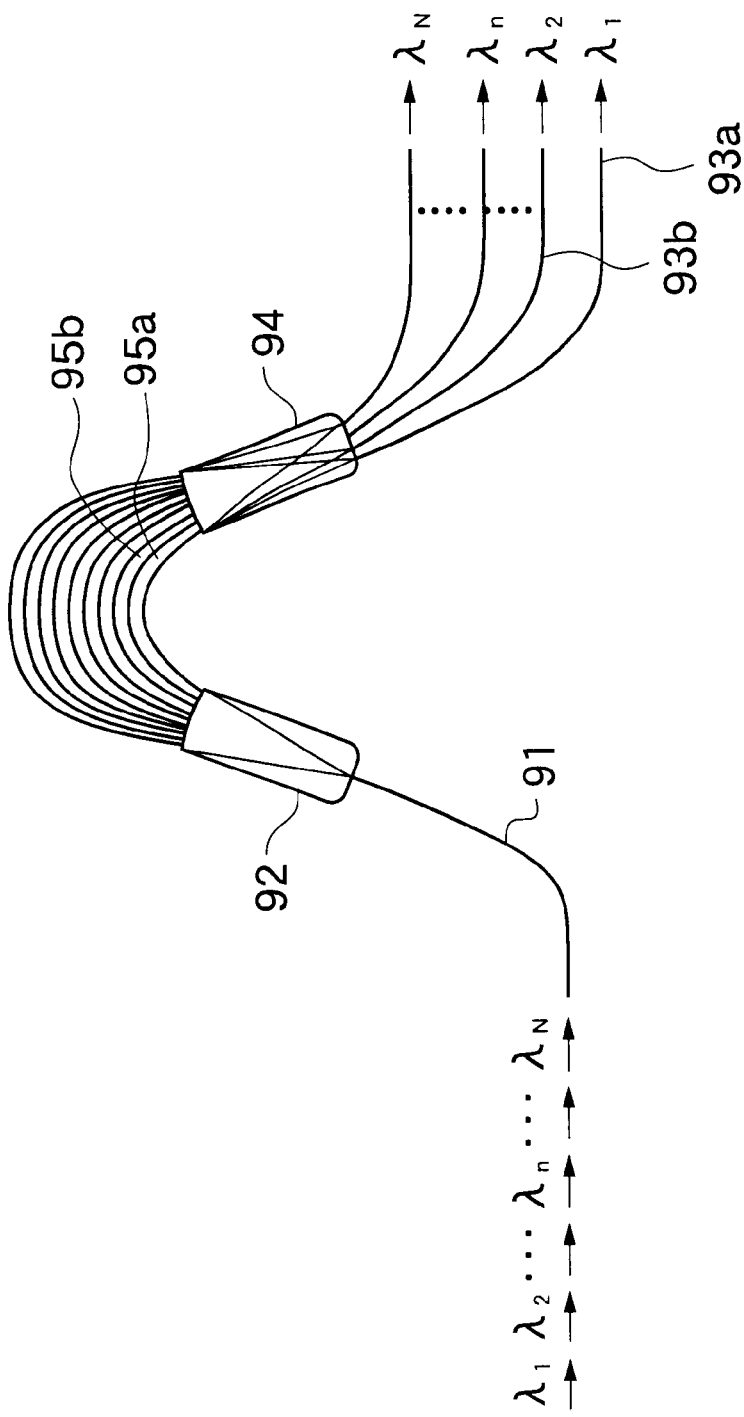
FIG. 3 is a diagram illustrating the constitution of an AWG spectrum-separating element.

Alternatively, as the spectrum-separating element 15, an AWG (array waveguide grating) spectrum-separating element may be used. FIG. 3 shows the constitution of the AWG spectrum-separating element.

As for the AWG spectrum-separating element, generally, an array waveguide grating included in a planar lightwave circuit (PLC) is used. As shown in FIG. 3, the array waveguide grating is constituted by connecting an input-side slab waveguide 92, which is connected with one input waveguide 91, with an output-side slab waveguide 94, which is connected with plural output waveguides 93a, 93b, ... by means of plural array waveguides 95a, 95b, ... having a predetermined difference in waveguide length.

The input-side slab waveguide 92 has a sector-like form having a center of curvature at an end of the input waveguide 91. Also, the output-side slab waveguide 94 has a sector-like form having a center of curvature at an end of the plural output waveguides 93a, 93b, ... . The plural array waveguides 95a, 95b, ... are disposed radially so that each optical axis goes through both of the centers of curvature of the input-side slab waveguide 92 and the output-side slab waveguide 94. Owing to this, the input-side slab waveguide 92 and the output-side slab waveguide 94 provide function same as a lens.

An incident light having plural different wavelengths $\lambda_1$–$\lambda_N$ enters the input waveguide 91 and is guided into the plural array waveguides 95a, 95b, ... by means of the lens function of the array waveguide 92. The plural wavelength components included in the incident light are exited in the array waveguide path 95a, 95b, ... and are guided into the plural output waveguides 93a, 93b, ... having waveguide lengths corresponding to the respective wavelengths.

Now, referring to FIG. 2 again, the photodetector 16 detects plural wavelength components which have been spectrum-separated by the spectrum-separating element 15. As for the photodetector 16, a two-dimensional photoelectric converter, in which a plurality of photoelectric converting elements are disposed two-dimensionally, and is capable of detecting the incident light separately on the basis of the position thereof, is used. For example, a PDA (photodiode array), a MOS-type sensor or the like may be used. Alternatively, a programmable two-dimensional sensor such as a CCD (charge coupled device) may be used.

These optical elements are disposed so that a component having a predetermined wavelength included in a light beam, which is reflected from a predetermined minute area of the ultrasonic detecting element, enters a predetermined photoelectric converting element of the photodetector 16. In the first embodiment, the light beams $L_1, L_2, \ldots$ output from the optical fibers $OF_1, OF_2, \ldots$ which are connected to the different areas of the ultrasonic detecting element, are respectively related to the first column, the second column, ... of the photoelectric converting elements which are disposed two-dimensionally. Also, the wavelengths $\lambda 1, \lambda 2$, ... of the spectrum-separated components are respectively coupled with the first column, the second column ... of the photoelectric converting element. By arranging an optical system so that the above-described relationship is obtained, a signal, which is output from a photoelectric converting element positioned at the n-th row and m-th column in the photodetector 16, is identified as a component having a wavelength $\lambda_n$ included in a light beam $L_m$ which is output from the optical fiber $OF_m$.

Figure 4:
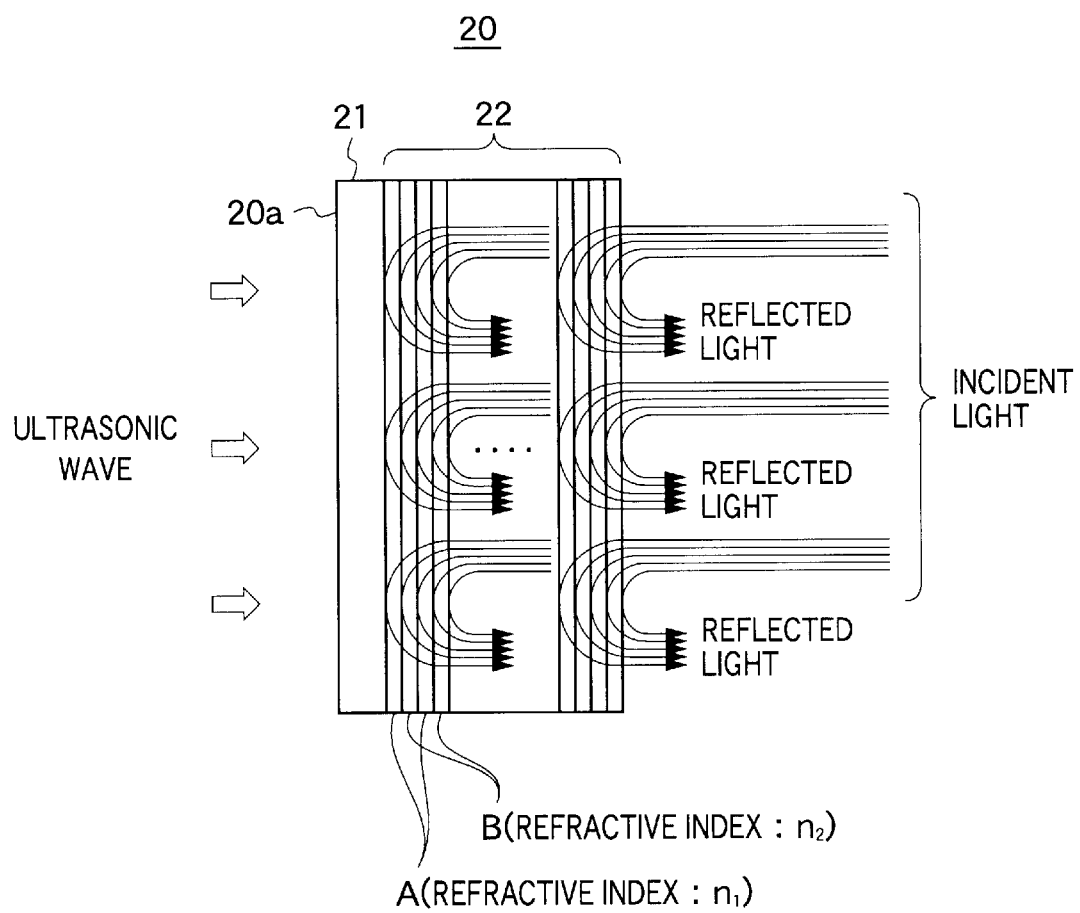
FIG. 4 is a diagram for explaining the principle of ultrasonic detection of an ultrasonic detecting element as shown in FIG. 2.

Next, referring to FIG. 4, the structure of the ultrasonic detecting element 20 and the detecting principle of the ultrasonic wave will be described in detail. The ultrasonic detecting element 20 is a multi-layered sensor including a substrate 21 and a multi-layered film 22 laminated on the substrate.

The substrate 21 is a film-like substrate that generates distortion by receiving ultrasonic wave and has, for example, a circular configuration of approximately 2 cm in diameter or a larger area. Formed on the substrate 21 is a multi-layered film 22 having a Bragg grating structure. The multi-layered film 22 is formed by alternately laminating two material layers which have the refractive indexes different from each other. In FIG. 4, material layers A having a refractive index $n_1$ and material layers B having a refractive index $n_2$ are shown Assuming that a pitch (distance) of a periodical structure of the multi-layered film 22 is "d", and that the wavelength of the incident light is "$\lambda$", the reflection condition of Bragg is expressed by the following formula.

$$2d \cdot \sin\theta = m\lambda \quad (1)$$

Herein, "$\theta$" denotes an angle formed between the incident plane and the incident light and "m" is arbitrary integer number. Assuming that $\theta=\pi/2$, the following formula is held.

$$2d = m\lambda \quad (2)$$

Bragg grating selectively reflects the light having a specific wavelength, which meets the reflection conditions of Bragg, and transmits the light having other wavelength.

When the ultrasonic wave is propagated to the ultrasonic detecting element 20, the substrate 21 is distorted accompanying the propagation of the ultrasonic wave, and the pitch "d" of the periodical structure changes at the respective positions of the multi-layered film 22. Accompanying this, the wavelength "λ" of the selectively reflected light changes. In the reflection characteristics of Bragg grating, there is an inclined band, where the optical reflectance changes, in the vicinity of a central wavelength under which an optical reflectance is the highest (i.e., an optical transmittance is the lowest). While allowing the light, which has a central wavelength within the range of the inclined band, to enter the multi-layered film 22, an ultrasonic wave is applied to the substrate 21. Then, it is possible to observe changes in the intensity of the reflected light (or transmitted light) corresponding to the intensity of the ultrasonic wave at the respective points on the receiving surface. By converting the changes in the intensity of the light into the intensity of the ultrasonic wave, two-dimensional strength distribution information of the ultrasonic wave can be obtained.

As for the material of the substrate 21, optical glass such as silica glass ($SiO_2$), BK7 (a product of SCHOTT), or the like is used. As for the substances used for the material layers A and B, a combination of substances having refractive indexes differ by 10% or more from each other is preferred. For example, a combination of $SiO_2$ and titanium oxide ($Ti_2O_3$), a combination of $SiO_2$ and tantalum oxide ($Ta_2O_5$), or the like is mentioned. Material layers A and B are formed on the substrate 21 by means of vacuum deposition, sputtering or the like.

In order to reduce the multiple reflection of the ultrasonic wave, it is effective to elongate the distance through which the ultrasonic wave propagates. When the ultrasonic wave propagates, not a little of the ultrasonic wave attenuates. The longer propagation distance results in the larger attenuation amount. Therefore, by ensuring enough propagation distance, it is possible to attenuate the ultrasonic wave satisfactorily before a time point when an ultrasonic wave, which is propagated to the one end, is reflected at the other end and returns to the one end. Accordingly, in the first embodiment, an optical fiber is used as the optical transmission path, and received ultrasonic wave is allowed to propagate through the optical fiber. That is, the optical transmission path has a function to pass the light therethrough and a function as the backing portion for attenuating the ultrasonic wave as well.

Figure 5:
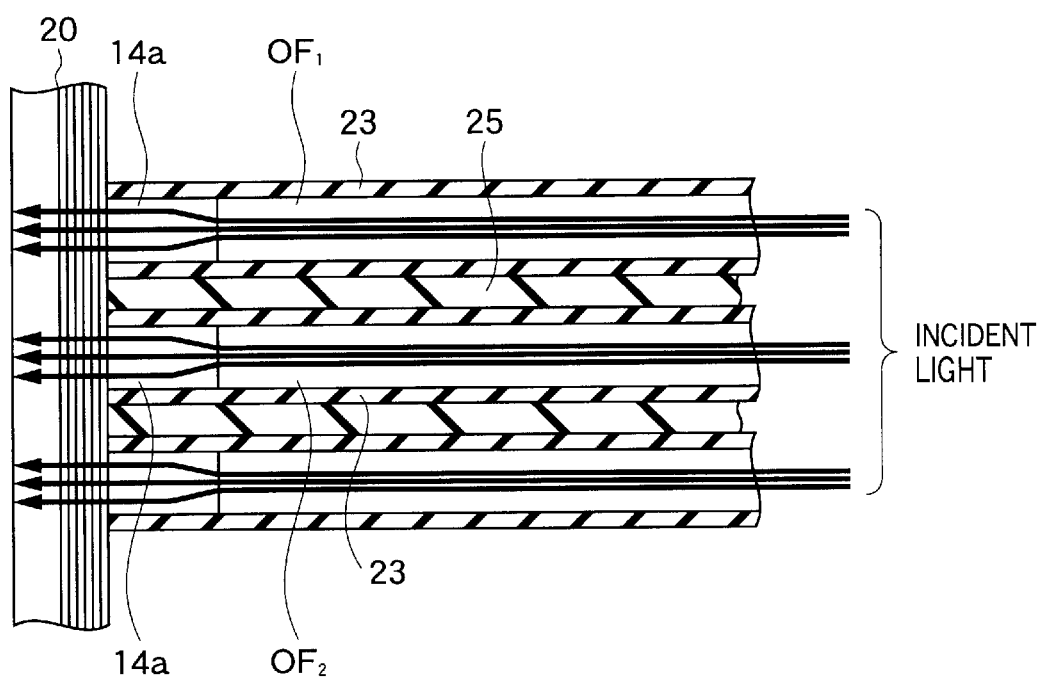
FIG. 5 is an expanded cross sectional view showing an ultrasonic detecting element, a collimating portion and a joint portion of optical transmission paths as shown in FIG. 2.

FIG. 5 is an expanded sectional view showing a part of optical transmission path 13, the collimating portion 14 and the ultrasonic detecting element 20 as shown in FIG. 2. As shown in FIG. 5, plural optical fibers $OF_1$, $OF_2$, . . . included in the optical transmission path (bundle fiber) 13 are connected to plural collimator lenses 14a included in the collimating portion (collimator lens array) 14 respectively with the optical axes thereof being aligned with each other. Further, plural collimator lens 14a are disposed in a two-dimensional state and connected to the ultrasonic detecting element 20. The plurality of optical fibers $OF_1$, OF2, . . . is bundled by using an adhesive agent 25.

The optical fibers $OF_1$, OF2, . . . are, for example, single mode or multi mode fibers of approximately 2 m in length and are covered with a member (covering material 23) including a resinous material having a low viscosity. In order to attenuate the ultrasonic wave during the propagation through the optical fiber, propagation energy loss of the ultrasonic wave is further increased by covering the optical fiber with the above member, resulting in earlier ultrasonic wave attenuation.

The lights transmitted in the optical fibers $OF_1$, $OF_2$, . . . are diffracted when the lights output from the optical fibers. Due to this, in the case where the optical fibers $OF_1$, OF2, . . . are connected directly to the ultrasonic detecting element 20, the lights are diffused resulting in an unsatisfactory interference within the ultrasonic wave detecting element. As a result, detection sensitivity of the ultrasonic detecting element becomes largely decreased. In order to avoid this phenomenon, the collimator lens 14a is connected at an end of each of the optical fibers $OF_1$, OF2, . . . to prevent the output light from being diffused. The collimating lens array including a plurality of collimator lenses 14a collimates the light guided by the respective optical fibers with respect to plural positions within an ultrasonic receiving plane of the ultrasonic detecting element 20.

As for the collimator lens 14a, a gradient index lens (hereinafter, abbreviated to GRIN lens) is used. The GRIN lens is known as, for example, the product name of Selfoc (registered trademark of NIPPON SHEET GLASS CO., LTD.) lens. The GRIN lens is a gradient refractive index type lens having a refractive index that differs depending on the position, and the optical characteristics thereof change by changing the length. For example, when the GRIN lens is adapted so that the length thereof is ¼ of a distance between an object and an image (a pitch under which the light focuses electing image), incident light is output in parallel light.

In the first embodiment, Selfoc lens array NA0.46 (a product of NIPPON SHEET GLASS CO., LTD.), in which a number of Selfoc lenses are disposed, is used at a length of 0.25L (L: a distance between an object and an image), and each Selfoc lens as a collimator lens 14a is connected to the optical fiber.

As shown in FIG. 5, the collimator lenses 14a may be covered with a covering material 23 in order to allow the ultrasonic wave to attenuate earlier as same as the case of the optical fibers $OF_1$, $OF_2$, . . . .

The optical fiber and the collimator lens, or, the collimator lens and the ultrasonic detecting element are connected to each other by means of a fusion bond or an adhesive agent. In the case of using the adhesive agent, it is preferred to use a resinous adhesive agent including epoxy series adhesives. The reason is as follows. In the adhesive agent as described above, since the acoustic impedance thereof is close to that of the members of the optical fiber and the collimator lens and the substrate of the ultrasonic detecting element, it is possible to prevent the ultrasonic wave from being reflected at each boundary of the respective members during the propagation. Also, as for the adhesive agent 25 for bundling the plurality of optical fibers, it is preferred to use a resinous adhesive agent including epoxy series adhesives. Because such adhesive agent can attenuate the ultrasonic wave, prevent cross talk of the ultrasonic wave between the neighboring optical fibers, and maintain the flexibility as a cable. In the first embodiment, STYCAST (a product of Emerson & Cuming) is used as the adhesive agent.

Figure 6:
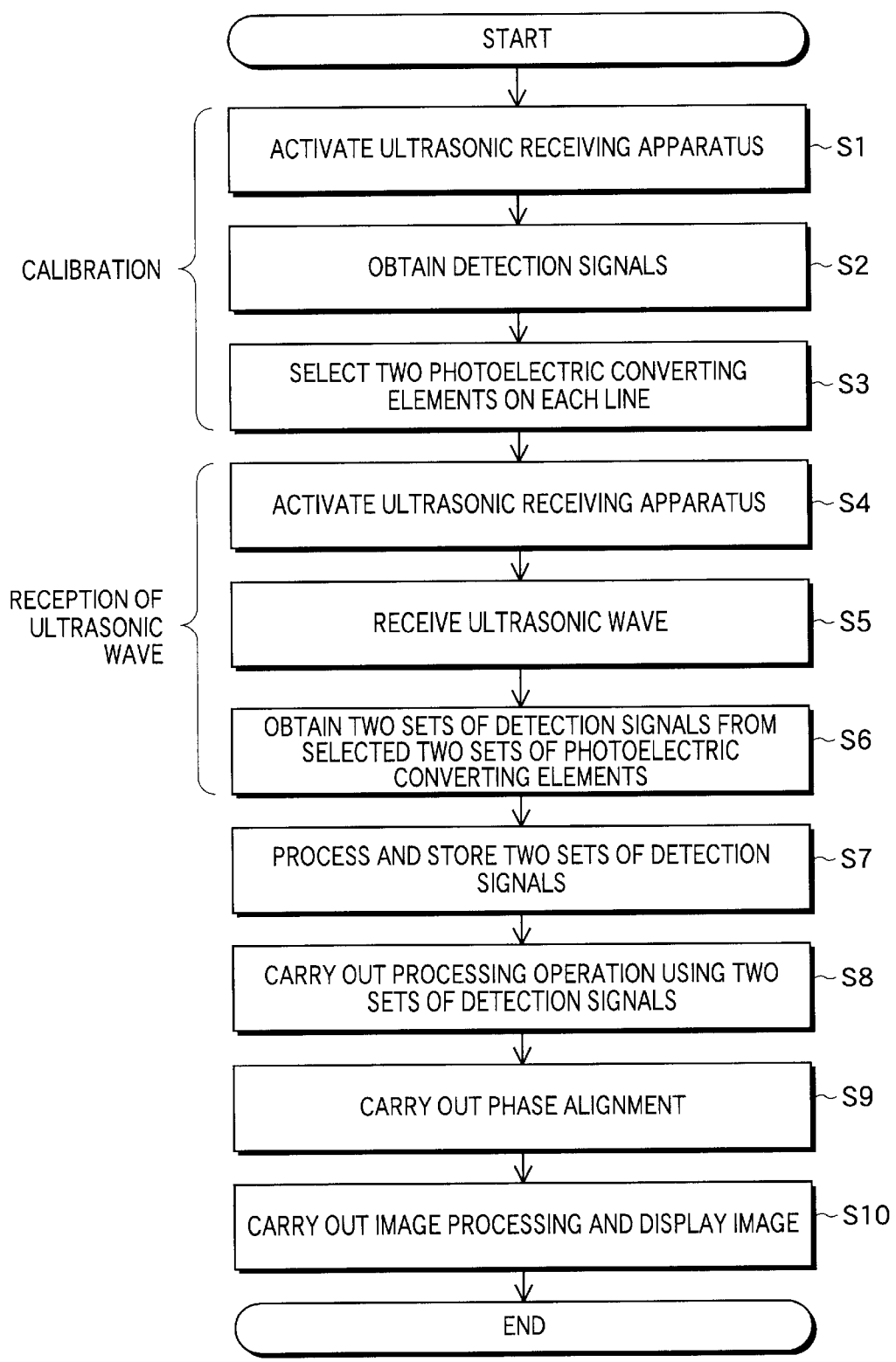
FIG. 6 is the flowchart showing the operation of an ultrasonic imaging apparatus including the ultrasonic receiving apparatus according to the first embodiment of the present invention.

Next, referring to FIG. 2, FIG. 6 and FIGS. 7A–7C, the operation of the ultrasonic receiving apparatus according to the first embodiment will be described. FIG. 6 is a flowchart illustrating the operation of an ultrasonic imaging apparatus including the ultrasonic receiving apparatus according to the first embodiment.

First of all, before receiving ultrasonic wave, a calibration is carried out to set up the wavelength of the light used for ultrasonic wave detection, that is, operation wavelength. Herein, the term "calibration" means an operation in which the reflection characteristics of the ultrasonic detecting element at certain time points are measured to determine the wavelength components to be adopted as the detection signals. In the first embodiment, pixel signals are generated by using a first detection signal and a second detection signal that are obtained from two predetermined wavelength components from among the plural wavelength components included in a broadband light. The ultrasonic detecting elements are extremely sensitive to the ambient circumstances such as temperature, humidity and the like, and the optical reflection characteristics are apt to change. For example, a central wavelength of a reflected light from the ultrasonic detecting element, which uses Bragg grating, changes at a rate of 0.01 nm/° C. Further, in the ultrasonic detecting elements having two-dimensional receiving plane, a structural fluctuation is included in each minute area of the receiving plane. Therefore, before receiving the ultrasonic wave, two operating wavelengths are set up for each minute area of the ultrasonic detecting element.

The calibration may be carried out any time after the reception of the ultrasonic wave has started.

Figure 7A:
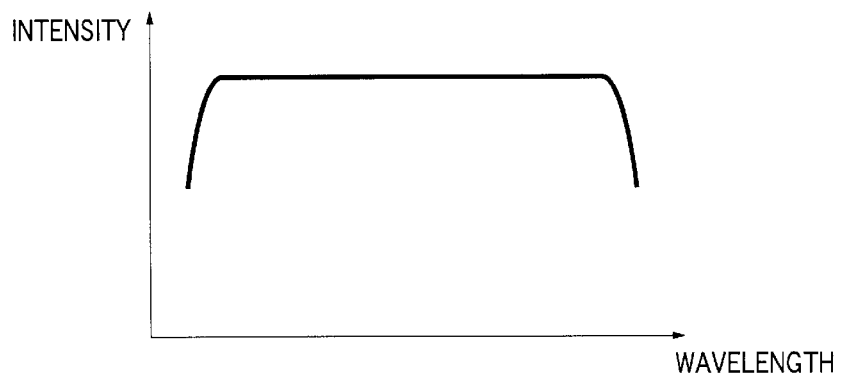
FIGS. 7A–7C are diagrams for explaining the operation of the ultrasonic receiving apparatus according to the first embodiment of the present invention.

At step S1, the ultrasonic receiving apparatus is activated. Then, for example, broadband light having the spectrum characteristics as shown in FIG. 7A is output from the light source 11. The light output from the light source passes through the collimator lens 17, the beam separator 12 and the collimator lens 18, and enters the optical fibers $OF_1$–$OF_M$ disposed on a line. The light transmitted via each optical fiber enters each minute area of the ultrasonic detecting element 20, and the light reflected in accordance with the optical reflectance of each minute area is output from the optical fiber. The light beams $L_1$–$L_M$, which are output from the optical fibers $OF_1$–$OF_M$, pass through the collimator lens 18 again, reflected by the beam separator 12, and enter the spectrum-separating element 15. The light beams $L_1$–$L_M$, are spectrum-separated by the spectrum-separating element 15, and each wavelength component enters the plurality of photoelectric converting elements included in the respective columns of the photodetector 16 in correspondence with the wavelength.

Figure 7B:
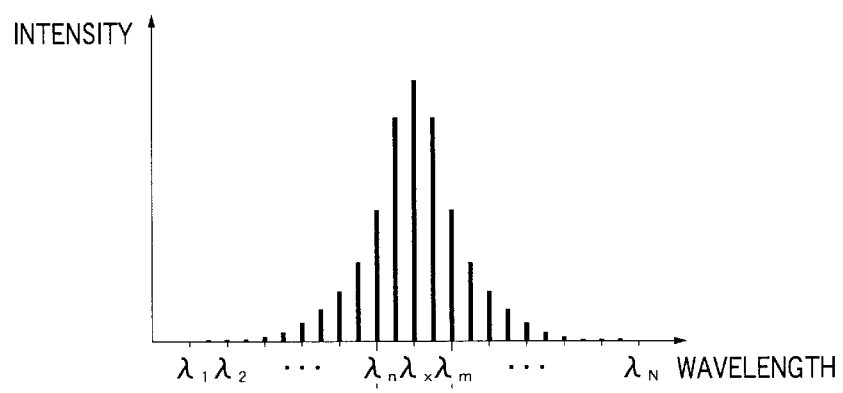

Owing to this, at step S2, detection signals of the photoelectric converting elements corresponding to the wavelengths $\lambda_1$–$\lambda_N$ are obtained from respective columns in the photodetector 16 corresponding to the light beams $L_1$–$L_M$. The signal output from each photoelectric converting element is converted into data by the TGC amplifier 51 and the A/D converter 52, and stored in the primary storage unit 53. FIG. 7B is a graph obtained on the basis of a signal output from a photoelectric converting element included in the m-th column in the photodetector 16. FIG. 7B shows a spectrum distribution of the light beam $L_m$, which has passed through the optical fiber $OF_m$ and reflected from the corresponding minute area of the ultrasonic detecting element. As shown in FIG. 7B, the light beam $L_m$ has the highest intensity at the wavelength $\lambda_x$ where the light beam is selectively reflected in accordance with the Bragg's reflection conditions.

Figure 7C:
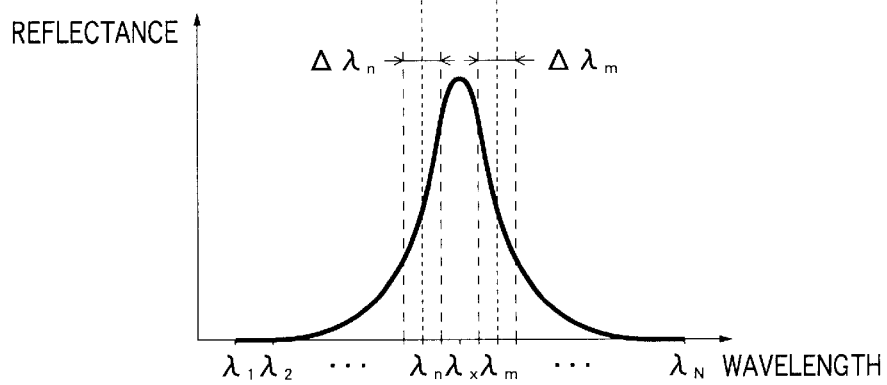

Then, at step S3, two photoelectric converting elements to be used for detection are selected on each column in the photodetector 16. As shown in FIG. 7C, the operating wavelength control unit 55 calculates optical reflection characteristics of each minute area on the basis of the signals obtained at step S2, determines plural wavelengths (operating wavelengths) to be used for detection based thereon, and selects two photoelectric converting elements where these wavelength components enter. As for the determination method of the operating wavelengths, a detailed description will be given later.

In the same manner as described above, on the plurality of columns where the light beams $L_1$, $L_2$, . . . output from the optical fibers $OF_1$, $OF_2$, . . . enters, the operating wavelengths. are set up by selecting two sets of photoelectric converting elements for obtaining the detection signals.

Then, the ultrasonic wave is received.

At step S4, the ultrasonic receiving apparatus is activated. Then, the broadband light output from the light source enters each minute area of the ultrasonic detecting element 20 via the optical fibers $OF_1$–$OF_M$. The light beams $L_1$–$L_M$ reflected from each minute area are spectrum-separated by the spectrum-separating element 15 and enter the photodetector 16.

Then, at step S5, an ultrasonic wave is transmitted from the ultrasonic transmitting unit 80 included in the ultrasonic imaging apparatus, and an echo wave reflected by an object to be inspected is received. Owing to this, the pitch of the periodical structure in each minute area of the ultrasonic detecting element 20 changes and the reflection characteristics of Bragg grating change. Therefore, the intensity of the light, which enters the photoelectric converting elements selected at step S3, also changes.

Then, at step S6, detection signals, which are output from at least selected two sets of photoelectric converting elements, are obtained. The photodetector 16 outputs detection signals from the photoelectric converting element, which is selected at step S3, to the signal processing unit 2 under the control of the operating wavelength control unit 55.

The detection signals obtained at step S6 are processed in the TGC amplifier 51 and the A/D converter 52 and stored in the primary storage unit 53 in time series (step S7).

Then, at step S8, the processor 56 performs processing operation by using the detection signals stored in the primary storage unit 53. The processing operation is carried out using the selected two sets of signals for one column of photoelectric converting elements included in the photodetector. The resultant signals represent signal (pixel signal) concerning one pixel. The processing operation will be described later in detail. These detection signals are stored again in the primary storage unit 53 in time series.

At step S9, the phase matching unit 54 performs a phase alignment on the detection signals stored after the above-described processing operation.

Further, at step S10, the phase-aligned signals are stored in the image memory 61 frame-by-frame, and further, reconstituted as a two-dimensional or three-dimensional data by the image processing unit 62, and then subjected to image processing such as interpolation, response modulation processing, gradation processing and so on. After that, images based on those signals are displayed on the graphic display unit 63.

Next, the setting of the operating wavelength and the processing of the detection signals will be described in detail.

FIG. 7C shows the reflection characteristics of Bragg grating in a minute area of an ultrasonic detecting element corresponding to a light beam Lm. As previously described, in these reflection characteristics, there are inclined bands $\Delta\lambda_n$ and $\Delta\lambda_m$, where the optical reflectance changes, in the vicinity of the central wavelength $\lambda_x$ where the optical reflectance is the highest. The intensity of the wavelength components $\lambda_n$ and $\lambda_m$ having the central wavelength within the inclined bands $\Delta\lambda_n$ and $\Delta\lambda_m$ is changed largely by geometrical changes of the ultrasonic detecting element caused by receiving the ultrasonic wave. That is to say, in the spectrum-separated area of the inclined band $\Delta\lambda_n$ and $\Delta\lambda_m$, large intensity changes can be observed. By converting the intensity changes into the intensity of the ultrasonic wave, it is possible to obtain information of the received ultrasonic wave. However, in the case where the intensity changes are too small, or, in the case where too large noises are included, accurate measurement cannot be achieved. Therefore, in the first embodiment, the obtained signals are subjected to processing operation in order to amplify the detection signal to increase the S/N ratio. Hereinafter, the processing operation will be described concretely.

Figure 8A:
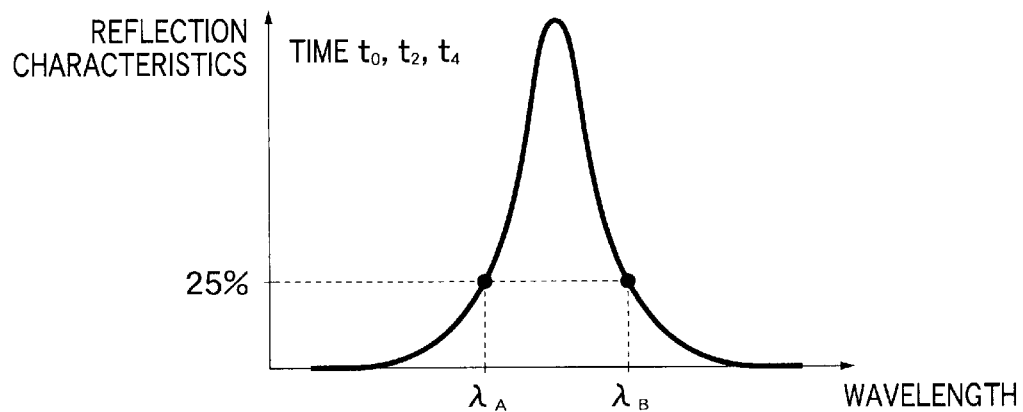
FIGS. 8A–8C are diagrams showing changes of optical reflection characteristics in the ultrasonic detecting element.
Figure 8B:
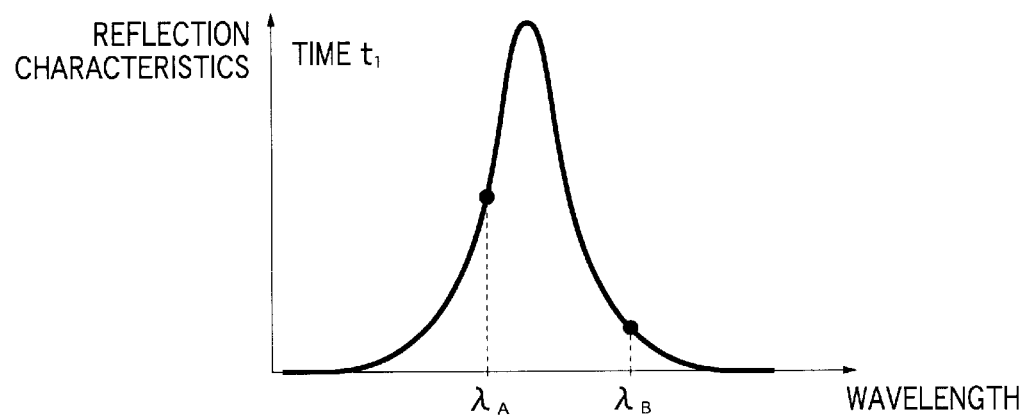
Figure 8C:
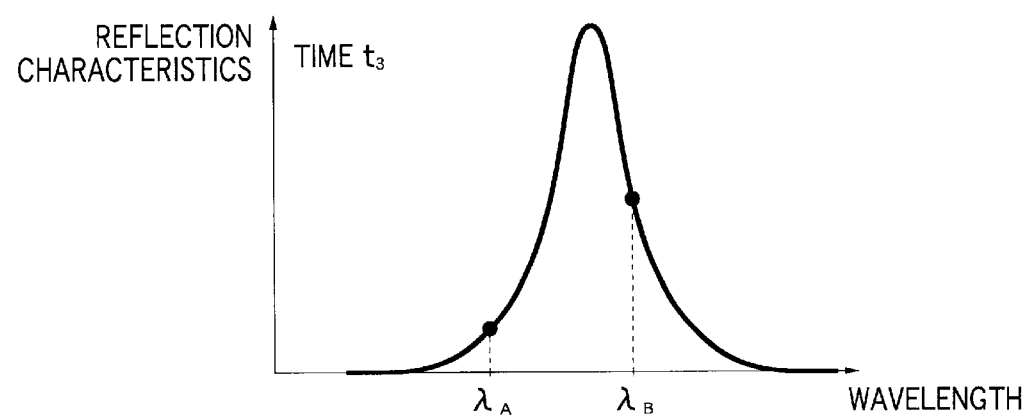
Figure 9A:
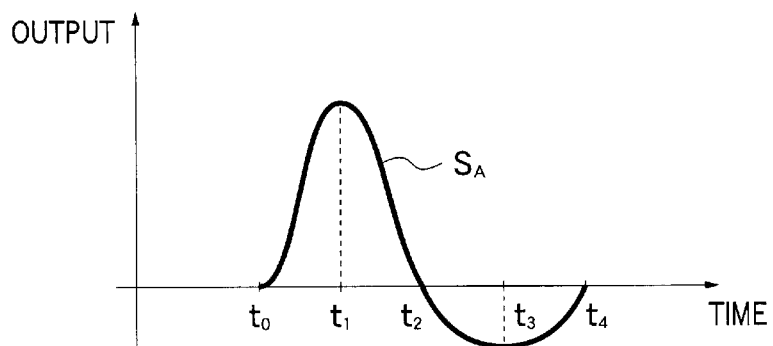
FIGS. 9A–9C are diagrams for explaining a signal processing method in the operation of the ultrasonic receiving apparatus according to the first embodiment of the present invention.
Figure 9B:
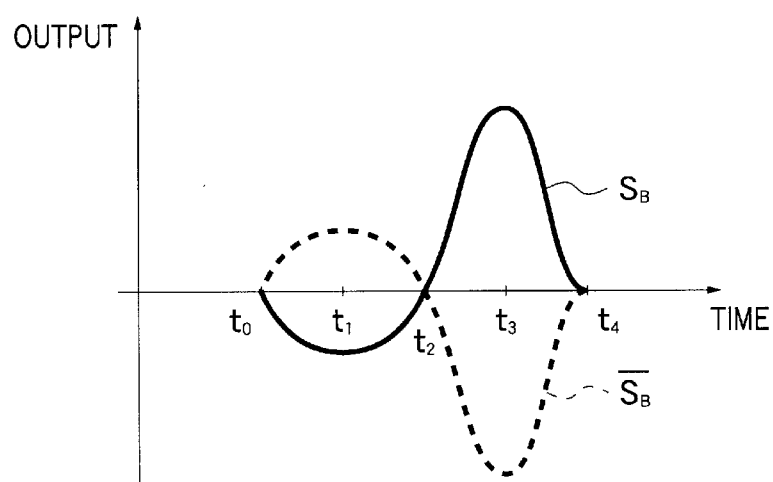

(1) In the Case of Selecting a Plurality of Wavelengths Having Equal Optical Reflectance As shown in FIG. 8A, the wavelength components $\lambda_A$ and $\lambda_B$ having predetermined optical reflectance of, for example, 25% at both sides of the central wavelength $\lambda_X$, where an optical reflectance is the highest, are determined as the operating wavelength. When an ultrasonic wave is received, the reflection characteristics change as shown in FIGS. 8A–8C in the period of time $t_0$–$t_4$. Accompanying this, the intensity of each wavelength components $\lambda_A$ and $\lambda_B$ changes as shown in FIGS. 9A and 9B. Herein, FIG. 9A shows a waveform of the detection signal $S_A$ representing the intensity of the wavelength component $\lambda_A$, and FIG. 9B shows a waveform of the detection signal $S_B$ representing the intensity of the wavelength component $\lambda_B$.

Figure 9C:
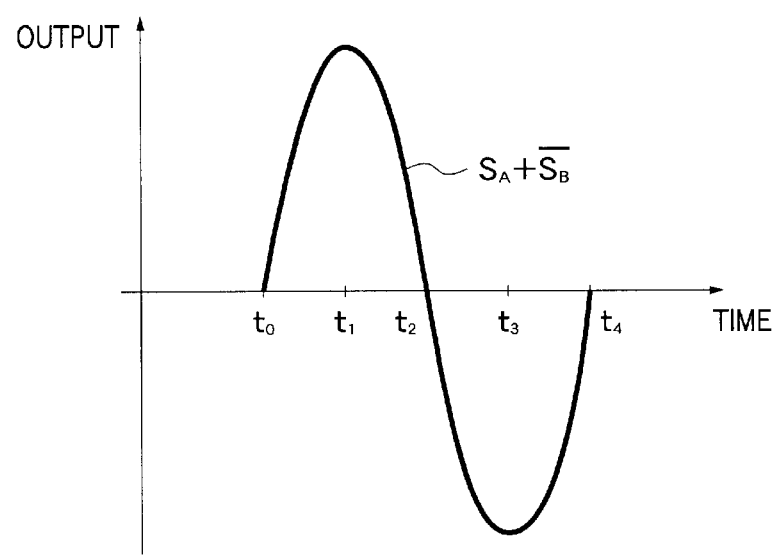

When the wavelengths $\lambda_A$ and $\lambda_B$ at both sides of the wavelength $\lambda_X$ are selected as the operating wavelength, signals having amplitudes of the same absolute value and opposite phases are obtained as shown in FIGS. 9A and 9B. Therefore, in this case, the phase of either one of the signals is inverted and then, both are added to each other. For example, as shown in FIG. 9B, an inversion signal $S_B$-bar of a detection signal $S_B$ is obtained and then, a detection signal $S_A$ and the inversion signal $S_B$-bar are added to each other as shown in FIG. 9C. The resultant signal is obtained as a pixel signal.

Herein, assuming that the absolute values of the amplitude of the signals $S_A$ and $S_B$ are $|s_A|$ and $|s_B|$, and the noises thereof are $N_A$ and $N_B$ respectively, the added signal amplitude is held as $|s_A|+|s_B|$, and the added noise level is held as $(N_A^2+N_B^2)^{1/2}$. Accordingly, the S/N ratio is expressed by the following formula:

$$S/N=(|s_A|+|s_B|)/(N_A^2+N_B^2)^{1/2}$$

Herein, since the absolute values of the amplitude of both signals are equal to each other, the following is obtained:

$$S/N=2\cdot|s_A|/(2N_A^2)^{1/2}=2^{1/2}\cdot|s_A|/N_A$$

As described above, when the detection signal $S_A$ or $S_B$ is used separately as a pixel signal, the S/N ratio is $S_A/N_A$ or $S_B/N_B$. However, by carrying out the processing operation using a plurality of signals, the S/N ratio increases to, for example, $2^{1/2}$ times thereof. Further, in the signal obtained by the processing operation, since the added signal amplitude becomes almost constant, the following merit is obtained. That is, even when the initial condition of the reflection characteristics has been shifted due to temperature changes or the like, the signal is hardly affected by level fluctuation and waveform deformation due to temperature changes or the like.

Figure 10A:
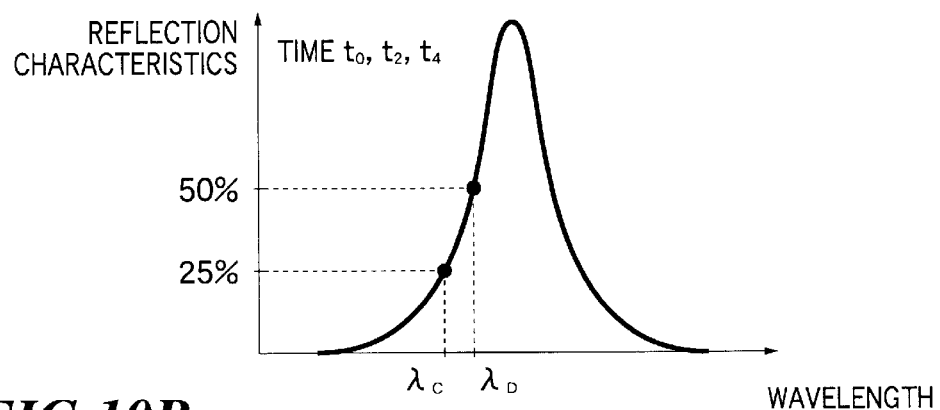
FIGS. 10A–10C are diagrams showing changes of optical reflection characteristics in the ultrasonic detecting element.
Figure 10B:
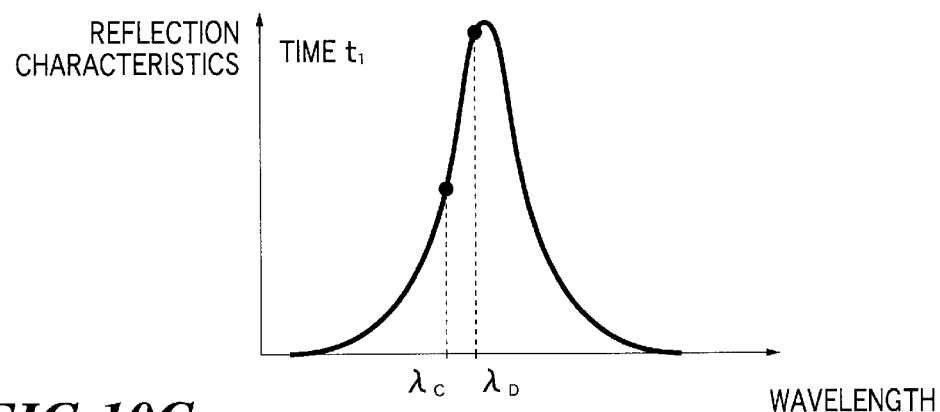
Figure 10C:
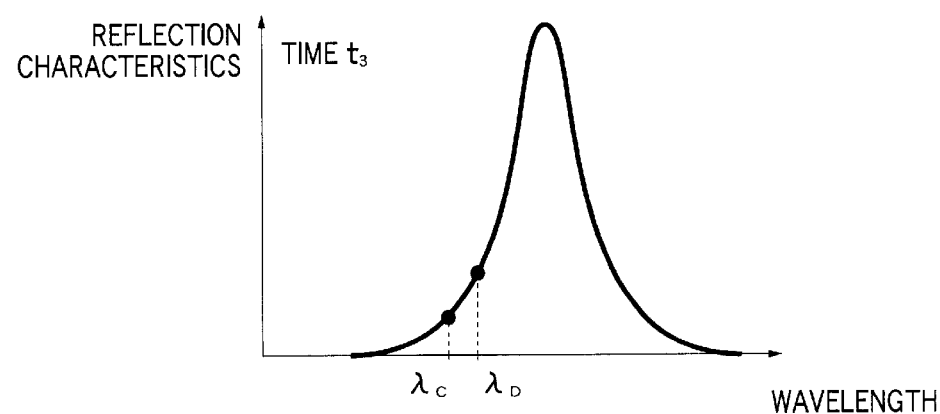
Figure 11A:
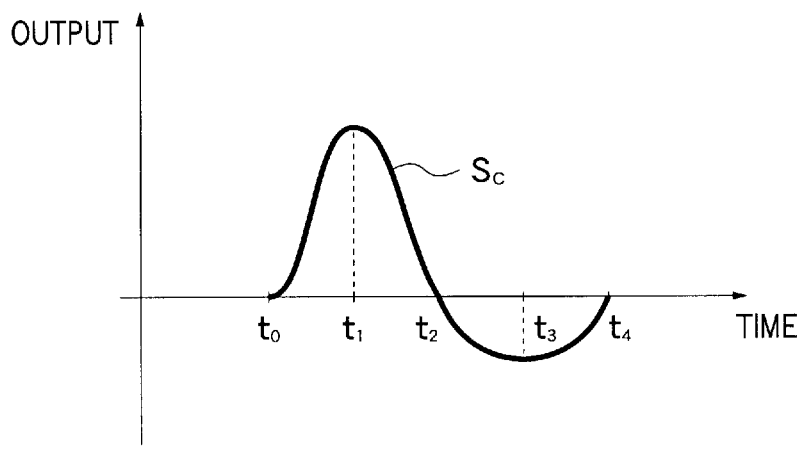
FIGS. 11A–11C are diagrams for explaining another signal processing method in the operation of the ultrasonic receiving apparatus according to the first embodiment of the present invention.
Figure 11B:
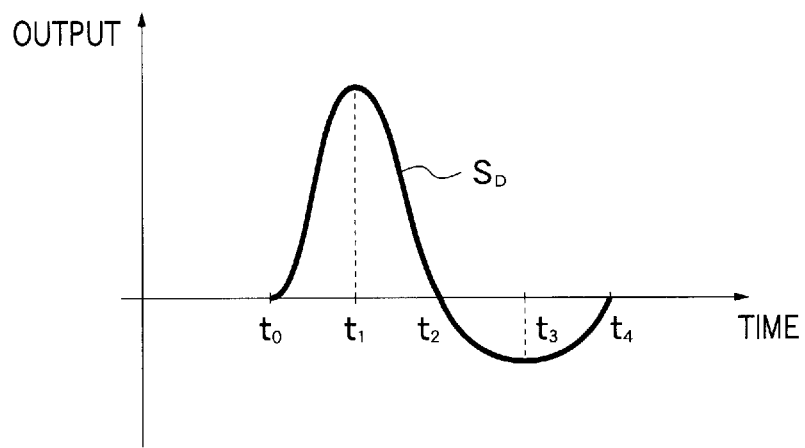
Figure 11C:
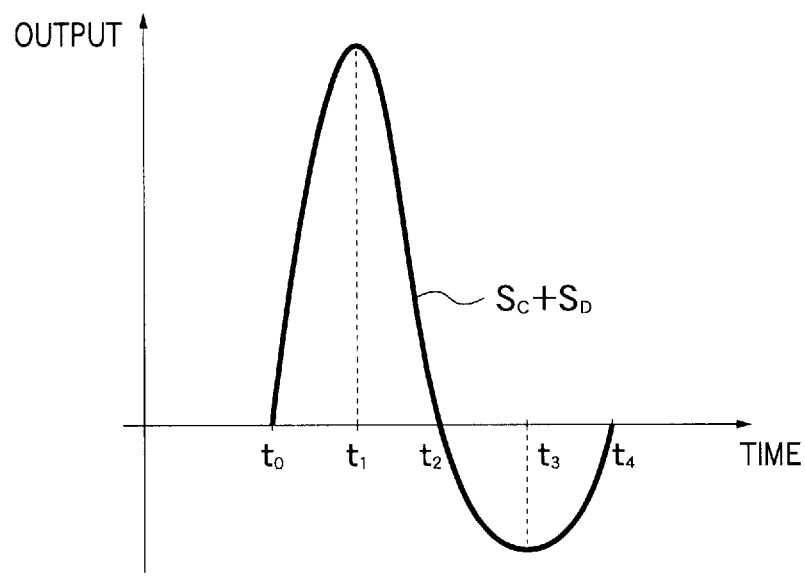

(2) In the Case of Selecting Plural Wavelengths Having Different Optical Reflectance As shown in FIG. 10A, wavelengths having different optical reflectance, for example, 25% and 50% are determined as the operating wavelength. When wavelengths $\lambda_C$ and $\lambda_D$ at the same side of the wavelength $\lambda_X$ are selected as the operating wavelengths, the reflection characteristics change as shown in FIGS. 10A–10C by receiving an ultrasonic wave, and as a result, detection signals $S_C$ and $S_D$ having the same phase are obtained as shown in FIGS. 11A and 11B. In this case, a pixel signal can be obtained by simply adding the detection signal $S_C$ to the detection signal $S_D$ as shown in FIG. 11C.

In the first embodiment, a single pixel signal is obtained by processing two detection signals obtained from two wavelength components included in one light beam. The same processing operation may be made using three or more detection signals obtained from three or more wavelength components.

Figure 12:
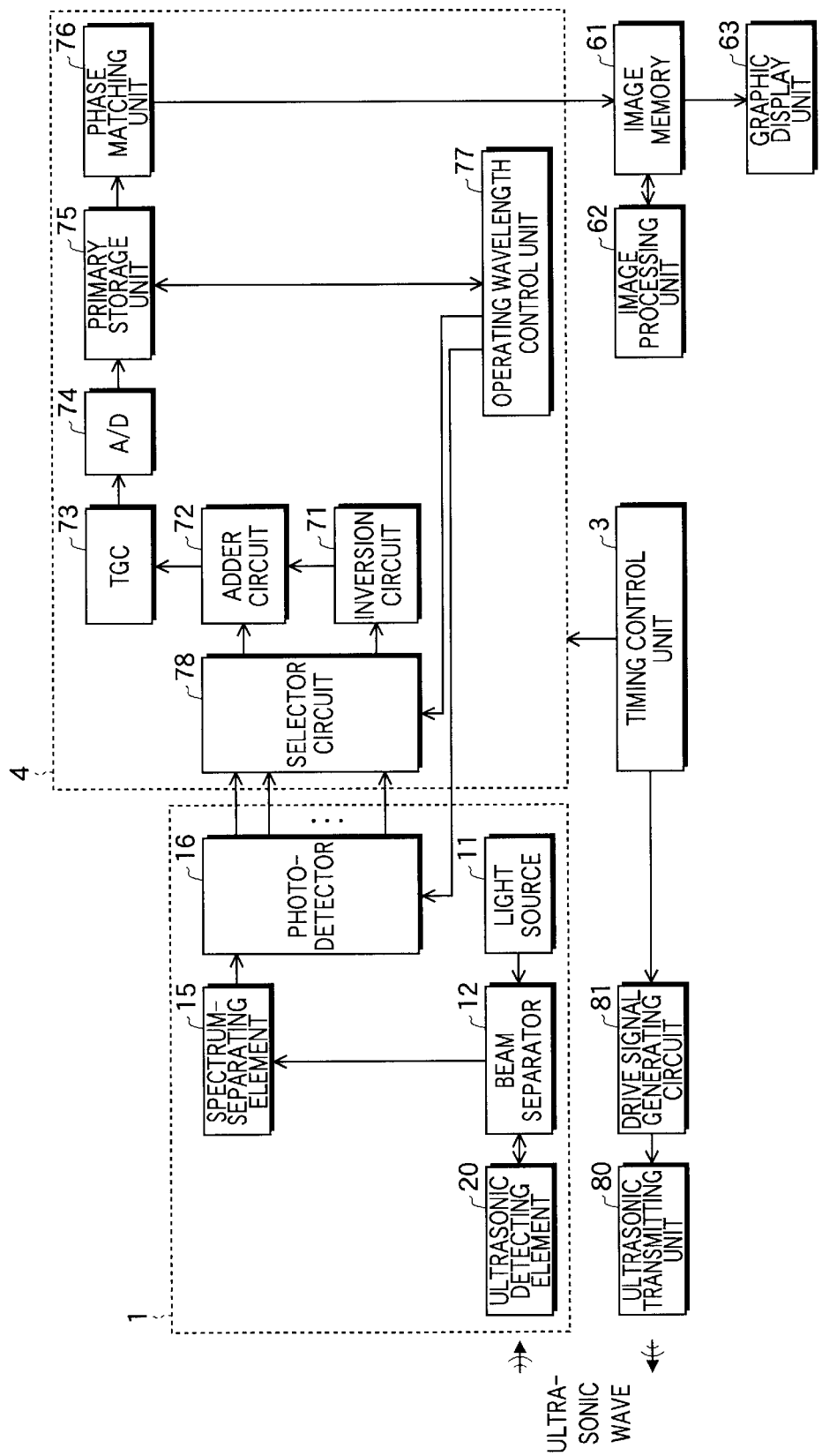
FIG. 12 is a block diagram showing the configuration of an ultrasonic imaging apparatus to which an ultrasonic receiving apparatus according to a second embodiment of the present invention is applied.

Next, referring to FIG. 12, an ultrasonic receiving apparatus according to a second embodiment of the present invention will be described. FIG. 12 is a block diagram showing the ultrasonic imaging apparatus to which an ultrasonic receiving apparatus according to the second embodiment is applied.

As shown in FIG. 12, the ultrasonic imaging apparatus has a signal processing unit 4 in place of the signal processing unit 2 in the first embodiment. The ultrasonic receiving apparatus according to the second embodiment comprises the ultrasonic receiving unit 1, the signal processing unit 4 and the timing control unit 3. The second embodiment is different from the first embodiment in the operation of the signal processing. The constitution other than the above is the same as that of the first embodiment.

The signal processing unit 4 includes an inversion circuit 71, an adder circuit 72, a TGC amplifier 73, an A/D converter 74, a primary storage unit 75, a phase matching unit 76, an operating wavelength control unit 77 and a selector circuit 78.

Under the control of the operating wavelength control unit 77, the selector circuit 78 selects two sets of detection signals from plural detection signals which are output from a plurality of photoelectric converting elements of the photodetector 16. The inversion circuit 71 inverts a first set of detection signals that are selected by the selector circuit 78 and outputs the inverted signals. The adder circuit 72 adds the first set of detection signals, which have been inverted by the inversion circuit 71, to a second set of detection signals, which are input from the photoelectric converting element, respectively and outputs the resultant signals. These circuits may be constituted of, for example, an operation amplifier or the like.

The TGC amplifier 73 amplifies the signals output from the adder circuit 72 while changing the gain corresponding to the detection time so as to adjust the attenuation of the ultrasonic wave within the object to be inspected. The A/D converter 74 converts the signals, which have been amplified by the TGC amplifier 73, into digital signals. The primary storage unit 75 stores the signals output from the A/D converter 74 in time series. The phase matching unit 76 aligns the phase by performing processing operation based on the signals stored in the primary storage unit 75. The operating wavelength control unit 77 selects a plurality of photoelectric converting elements, upon which the operation wavelength components are incident, for each column included in the photodetector 16, and controls the photodetector 16 or the signal processing unit 3 so that the detection signals output from the selected photoelectric converting elements are input into the adder circuit 72 or the inversion circuit 71.

Next, referring to FIGS. 12–14C, the operation of the ultrasonic receiving apparatus according to the second embodiment will be described. FIG. 13 is a flowchart showing the operation of the ultrasonic imaging apparatus including the ultrasonic receiving apparatus according to the second embodiment.

In the second embodiment, a calibration is carried out in the same manner as steps S1–S3 in the first embodiment, and an ultrasonic wave is received in the same manner as steps S4–S6 to obtain detection signals from the selected plurality of photoelectric converting elements. Herein, wavelengths $\lambda_A$ and $\lambda_B$ as shown in FIGS. 8A–8C are selected as the operating wavelengths.

Figure 14A:
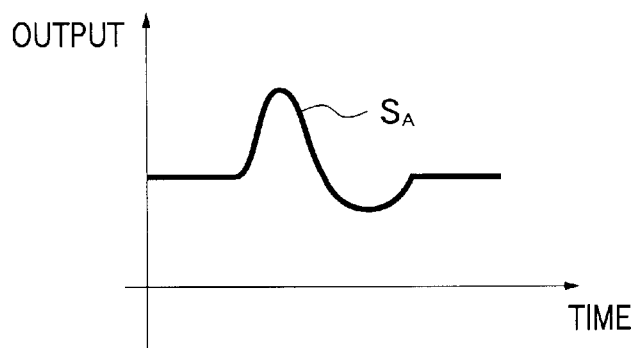
FIGS. 14A–14C are diagrams for explaining signal processing method in the operation of the ultrasonic receiving apparatus according to the second embodiment of the present invention.
Figure 14B:
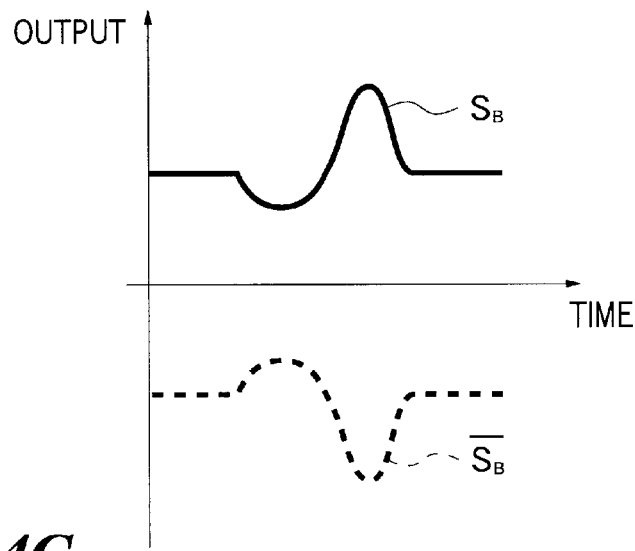

At step S21, the inversion circuit 71 inverts a first set of the detection signals output from the predetermined photoelectric converting elements. Then, at step S22, the adder circuit 72 inputs the first set of the detection signals, which have been inverted by the inversion circuit 71, and a second set of detection signals, which are output from another predetermined photoelectric converting elements, and adds the inverted first set of the detection signals to the second set of detection signals respectively to output the resultant signals. Wherein, FIG. 14A shows a waveform of the detection signal $S_A$ corresponding to a wavelength component $\lambda_A$. Also, FIG. 14B shows a waveform of the detection signal $S_B$ corresponding to a wavelength component $\lambda_B$, and a broken line in FIG. 14B shows a waveform of an inversion signal $S_B$-bar. Furthermore, FIG. 14C shows a waveform of a signal in which the detection signal $S_A$ and the inversion signal $S_B$-bar are added to each other.

At step S23, signals output from the adder circuit 72 are subjected to the signal processing by the TGC amplifier 73 and A/D converter 74, and are stored in the primary storage unit 75 in time series. Then, the signals stored in the primary storage unit 75 are subjected to the phase alignment by the phase matching unit 76.

Further, same as the first embodiment, the phase-aligned signals are stored in the image memory 61 frame-by-frame. Then, the signals are reconstituted into two-dimensional or three-dimensional data in the image processing unit 62, and are subjected to the image processing such as interpolation, response modulation processing, gradation processing and the like, and finally images based on the signals are displayed on the graphic display unit 63 at step S10.

Figure 14C:
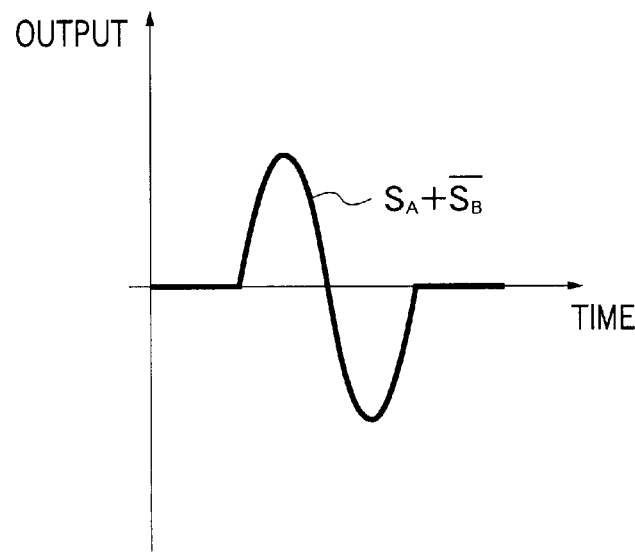

According to the second embodiment, since analog signals are added, the AC component included in the signal is amplified, and the DC component is approximated to zero as shown in FIG. 14C. Accordingly, a signal processing system such as an amplifier, ADC or the like having a smaller dynamic range works satisfactorily.

Figure 15:
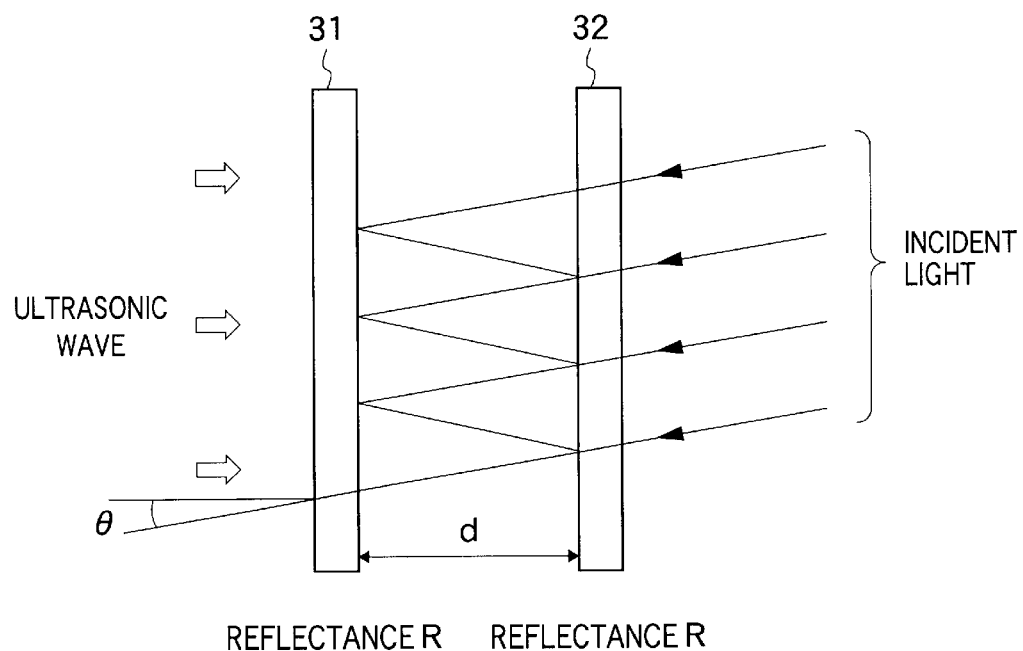
FIG. 15 is a diagram illustrating a modification of the ultrasonic receiving apparatus according to the first or second embodiment of the present invention.

The first or second embodiment of the present invention may be modified as described bellow. Referring to FIG. 15, the modification will be described. In this example, in place of the ultrasonic detecting element 20 in FIG. 2, an ultrasonic detecting element (etalon sensor) 30 as shown in FIG. 15 is used. The constitution other than the above is the same as that described referring to FIG. 1 or FIG. 12.

As shown in FIG. 15, a substrate 31 is a film-like substrate that is deformed by an ultrasonic wave. A substrate 32 is disposed facing to the substrate 31, and these substrates form a structure that is the same as an etalon.

Assuming that an optical reflectance of the substrates 31 and 32 is "R", the distance between these substrates is "d", and the wavelength of the incident light is "λ", an transmittance of the etalon is expressed as following:

$$T = (1 + 4R/(1-R)^2 \cdot \sin^2(\phi/2))^{-1} \quad (3)$$

$$\phi = 2\pi/\lambda \cdot 2nd \cdot \cos\theta \quad (4)$$

Herein, "θ" denotes an exit angle measured from the perpendicular line with respect to the exit plane and "n" is arbitrary integer number. Assuming that θ=0, the following formula is held.

$$\phi = 4\pi nd/\lambda \quad (5)$$

The etalon transmits the light having wavelength "λ" at an optical transmittance "T" and reflects the same at an optical reflectance R=(1−T).

When an ultrasonic wave is propagated to the ultrasonic detecting element 30, since the substrate 31 is distorted and the distance "d" between the substrates 31 and 32 is changed at respective positions of the receiving plane, the optical reflectance with respect to the light having the wavelength "λ" changes. Therefore, in the same manner as described referring to FIG. 6, a pre-detection is carried out. Photoelectric converting elements in the photodetector are selected, upon which light having a central wavelength in the area where a change of optical reflectance is large is incident. While allowing a broadband light to enter the photoelectric converting elements, an ultrasonic wave is applied to the substrate 31. Thereby, it is possible to measure the intensity change of each wavelength component in the reflected light corresponding to the intensity of the ultrasonic wave at respective position in the receiving plane. By carrying out the processing operation on the detection signals representing the wavelength components, it is possible to measure the intensity of the ultrasonic waves two-dimensionally.

Figure 16A:
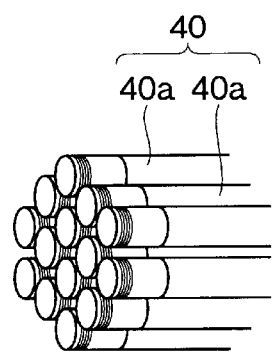
FIGS. 16A and 16B are diagrams illustrating other modifications of the ultrasonic receiving apparatus according to the first or second embodiment of the present invention.
Figure 16B:
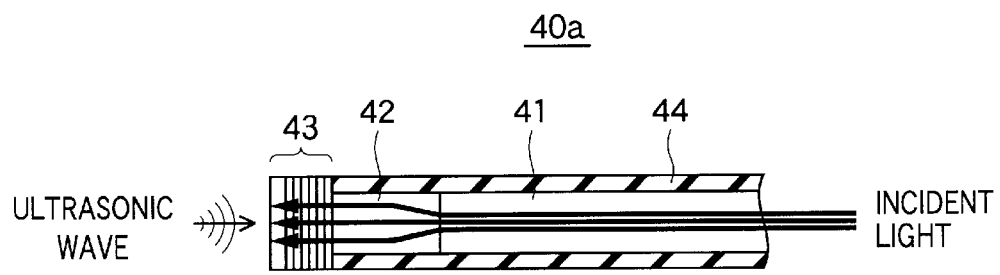

Referring to FIGS. 16A and 16B, another modification according to the first or second embodiment of the present invention will be described below. This modification uses, in place of the ultrasonic detecting element 20, the optical transmission path 13 and the collimating portion 14 as shown in FIG. 2, a bundle fiber 40 having ultrasonic sensing portions as shown in FIG. 16A. The constitution other than the above is the same as that described referring to FIG. 1 or FIG. 12.

FIG. 16B shows a constitution of plural fibers 40a included in the bundle fiber 40. Each of the plural fibers 40a includes an optical fiber 41 and a collimator lens 42. In the embodiment, a Selfoc lens having length of 0.25 L is used as a collimator lens 42, same as the first embodiment. The optical fiber 41 and the collimator lens 42 are connected to each other by means of a fusion bond or a resinous adhesive agent including epoxy series adhesives.

Formed at one end of the collimator lens 42 is a multi-layered film 43 in which two different material layers are laminated alternately. The multi-layered film 43 constitutes a Bragg grating structure and serves as the ultrasonic sensing portion. As for the material for the multi-layered film 43, for example, a combination of $SiO_2$ and titanium oxide ($Ti_2O_3$), or a combination of $SiO_2$ and tantalum oxide ($Ta_2O_5$), or the like is used. The material layer as described above is formed on the collimator lens 42 by means of vacuum deposition, sputtering or the like.

The fiber 40a is covered by a member (covering material 44) having a low viscosity so that the ultrasonic wave is attenuated before the ultrasonic wave propagated to one end of the fiber 40a is reflected at the other end thereof. Further, as shown in FIG. 16B, the covering material 44 may also cover the collimator lens 42. Thereby, the energy loss of the ultrasonic wave propagated to the fiber 40a can be made larger, so that an effect as a backing portion can be increased by allowing the ultrasonic wave to attenuate earlier.

By bundling a number of fibers 40a as described above using a resinous adhesive agent including epoxy series adhesives, the bundle fiber 40 having ultrasonic sensing portions is manufactured.

As described above, according to the present invention, since the processing operation is made using plural detection signals obtained by detecting plural wavelength components of the light that has been modulated in plural detection areas of the ultrasonic detecting element respectively, the S/N ratio of the detection signals can be increased. These detection signals are obtained by obtaining the reflection characteristics of the ultrasonic detecting elements by means of calibration to select the photoelectric converting elements, which are to be used for detecting the ultrasonic wave, on the basis of the reflection characteristics. Accordingly, even when the reflection characteristics change due to the ambience such as temperature, humidity, or the like, it is possible to reduce fluctuation of the sensitivity and also suppress variation of sensitivities in plural minute areas caused by structural distortion of the ultrasonic detection elements, thereby maintain high detection sensitivity. Further, in the case where a broadband light is used, the wavelength to be used for detecting the ultrasonic wave is selected from a spectrum-separated light of the broadband light, and therefore, it is not necessary to control the wavelength of the light in accordance with the ambience nor the detection area and it is not necessary to change the reflection characteristics for every detection area. Owing to this, it is possible to simplify and miniaturize the constitution of the ultrasonic receiving apparatus. Accordingly, the manufacture of the ultrasonic receiving apparatus becomes easier and cost reduction thereof is made possible.

What is claimed is:

1. An ultrasonic receiving apparatus comprising:

a light source for generating broadband light;

an ultrasonic detecting element including an ultrasonic sensing portion which is expanded and contracted by a received ultrasonic wave to change an optical reflectance thereof in accordance with expansion and contraction thereby performing intensity modulation of the light generated by said light source;

spectrum separating means for spectrum-separating the light intensity-modulated by said ultrasonic detecting element;

photo detecting means having a plurality of photoelectric converting elements for detecting the light spectrum-separated by said spectrum separating means for each of plural wavelength components to generate at least a first detection signal obtained by detecting a first wavelength component and a second detection signal obtained by detecting a second wavelength component; and processing means for carrying out processing operation using the first detection signal and the second detection signal so as to obtain information about the ultrasonic wave received by said ultrasonic detecting element.

2. The ultrasonic receiving apparatus according to claim 1, wherein said processing means adds the first detection signal and the second detection signal to each other after inverting the phase of either one thereof.

3. The ultrasonic receiving apparatus according to claim 1, further comprising:

controlling means for selecting two sets of photoelectric converting elements to be used for detecting ultrasonic wave from among the plurality of photoelectric converting elements of said photo detecting means on the basis of a detection result of said photo detecting means at a calibration mode, and controlling said processing means to carry out the processing operation using the first detection signal and the second detection signal output from the selected two sets of photoelectric converting elements respectively at a receiving mode.

4. The ultrasonic receiving apparatus according to claim 2, further comprising:

controlling means for selecting two sets of photoelectric converting elements to be used for detecting ultrasonic wave from among the plurality of photoelectric converting elements of said photo detecting means on the basis of a detection result of said photo detecting means at a calibration mode, and controlling said processing means to carry out the processing operation using the first detection signal and the second detection signal output from the selected two sets of photoelectric converting elements respectively at a receiving mode.

5. An ultrasonic receiving method comprising the steps of:

(a) allowing light to enter an ultrasonic detecting element including an ultrasonic sensing portion which is expanded and contracted by a received ultrasonic wave to change an optical reflectance thereof in accordance with expansion and contraction thereby performing intensity modulation of the incident light, spectrum-separating the light intensity-modulated by said ultrasonic detecting element and detecting the spectrum-separated light for each of plural wavelength components by using photo detecting means having a plurality of photoelectric converting elements to generate at least a first detection signal obtained by detecting a first wavelength component and a second detection signal obtained by detecting a second wavelength component with respect to each of plural detection areas of said ultrasonic detecting element; and (b) carrying out processing operation using the first detection signal and the second detection signal so as to obtain information about the ultrasonic wave received at each of the plural detection areas of said ultrasonic detecting element.

6. The ultrasonic receiving method according to claim 5, further comprising, prior to step (a), the step of (c) allowing light to enter said ultrasonic detecting element, spectrum-separating the light reflected from said ultrasonic detecting element and detecting the spectrum-separated light for each of the plural wavelength components by using said photo detecting means so as to select two sets of photoelectric converting elements to be used for detecting an ultrasonic wave from among a plurality of photoelectric converting elements of said photo detecting means, wherein:

step (a) includes generating a first detection signal and a second detection signal for each of plural detection areas of said ultrasonic detecting element by using the two sets of photoelectric converting elements selected at step (c).

* * * * *